(12) United States Patent
Sederoff et al.

(10) Patent No.: US 8,039,438 B2
(45) Date of Patent: Oct. 18, 2011

(54) SYNTHETIC PEPTIDES THAT CAUSE F-ACTIN BUNDLING AND BLOCK ACTIN DEPOLYMERIZATION

(75) Inventors: Heike Sederoff, Raleigh, NC (US); Steven C Huber, Savoy, IL (US); Carolyn A Larabell, Berkeley, CA (US)

(73) Assignees: The Regents of the University of California, Oakland, CA (US); North Carolina State University, Raleigh, NC (US); U.S. Department of Agricultue/NCAUR, Washington, DC (US)

( * ) Notice: Subject to any disclaimer, the term of this patent is extended or adjusted under 35 U.S.C. 154(b) by 1023 days.

(21) Appl. No.: 10/576,757

(22) PCT Filed: Oct. 20, 2004

(86) PCT No.: PCT/US2004/034996
§ 371 (c)(1),
(2), (4) Date: Apr. 20, 2006

(87) PCT Pub. No.: WO2005/040193
PCT Pub. Date: May 6, 2005

(65) Prior Publication Data
US 2008/0280358 A1 Nov. 13, 2008

Related U.S. Application Data

(60) Provisional application No. 60/513,275, filed on Oct. 20, 2003.

(51) Int. Cl.
*A61K 38/08* (2006.01)
*A61K 38/10* (2006.01)
*C07K 7/06* (2006.01)
*C07K 7/08* (2006.01)

(52) U.S. Cl. .................. 514/19.3; 514/19.8; 514/21.4; 514/21.5; 514/21.6; 514/21.7; 514/21.8; 530/326; 530/327; 530/328; 530/329

(58) Field of Classification Search .................. None
See application file for complete search history.

(56) References Cited

U.S. PATENT DOCUMENTS

| 6,043,339 | A | 3/2000 | Lin et al. |
| 6,472,507 | B1 | 10/2002 | Fischer et al. |
| 6,476,212 | B1 | 11/2002 | Lalgudi et al. |
| 6,596,925 | B1 | 7/2003 | Perera et al. |

(Continued)

OTHER PUBLICATIONS

Sebkova, Veronika et al., Biochemical, Physiological, and Molecular Characterization of Sucrose Synthase from Daucus carota, Plant Physiology, 1995, vol. 108, pp. 75-83.

(Continued)

*Primary Examiner* — Jeffrey E Russel
(74) *Attorney, Agent, or Firm* — Michelle Chew Wong; Lawrence Berkeley; National Laboratory

(57) ABSTRACT

Synthetic peptides derived from sucrose synthase, and having homology to actin and actin-related proteins, sharing a common motif, useful for causing acting bundling and preventing actin depolymerization. Peptides exhibiting the common motif are described, as well as specific synthetic peptides which caused bundled actin and inhibit actin depolymerization. These peptides can be useful for treating a subject suffering from a disease characterized by cells having neoplastic growth, for anti-cancer therapeutics, delivered to subjects solely, or concomitantly or sequentially with other known cancer therapeutics. These peptides can also be used for stabilizing microfilaments in living cells and inhibiting growth of cells.

12 Claims, 13 Drawing Sheets

| EN | GIVRK | WI | SRFEVW | PYL | KK |

$X_4$  $X_3$  $X_2$  $X_1$  $X_5$  $X_6$

| SEQ ID NO. | | SEQUENCE |
|---|---|---|
| SEQ ID NO:22 | $X_1$ | SRFEVW |
| SEQ ID NO:17 | $X_2$-$X_1$ | WISRFEVW |
| SEQ ID NO:14 | $X_1$-$X_5$ | SRFEVWPYL |
| SEQ ID NO:23 | $X_2$-$X_1$-$X_5$-$X_6$ | WISRFEVWPYLKK |
| SEQ ID NO:12 | $X_3$-$X_2$-$X_1$-$X_5$ | GIVRKWISRFEVWPYL |
| SEQ ID NO:10 | $X_3$-$X_2$-$X_1$-$X_5$-$X_6$ | GIVRKWISRFEVWPYLKK |
| SEQ ID NO:24 | $X_4$-$X_3$-$X_2$-$X_1$-$X_5$-$X_6$ | ENGIVRKWISRFEVWPYLKK |

U.S. PATENT DOCUMENTS

2004/0034888 A1* 2/2004 Liu et al. .................. 800/289

OTHER PUBLICATIONS

Winter, Heike et al., Identification of sucrose synthase as an actin-binding protein, Federation of European Biochemical Societies Letters, 1998, vol. 430, pp. 205-208.

Huang, Xiao-Fang et al., Complete Nucleotide Sequence of the Maize (*Zea mays* L.) Sucrose Synthase 2 cDNA, Plant Physiology, 1994, vol. 104, pp. 293-294.

Tellam, Ross L. et al., A common theme in the amino acid sequences of actin and many actin-binding proteins?, Trends in Biochemical Science, Apr. 1989, vol. 14(4), pp. 130-133.

Manseau, Lynn J. et al., Molecular and Genetic Characterization of the *Drosophila melanogaster* 87E Actin Gene Region, Genetics, 1988, vol. 119(2), pp. 407-420.

Fryberg, Eric A. et al., The Actin Genes of *Drosophila*: Protein Coding Regions Are Highly Conserved but Intron Positions Are Not, Cell, 1981, vol. 24(1), pp. 107-116.

Morris, May C. et al., A peptide carrier for the delivery of biologically active proteins into mammalian cells, Nature Biotechnology, Dec. 2001, vol. 19, pp. 1173-1176.

* cited by examiner

Fig. 1A

| | | | |
|---|---|---|---|
| SUS1 | SEQ ID NO: 2 | ENGILRKWISRFDVW | native |
| SUS2 | SEQ ID NO: 3 | ENGIVRKWISRFEVW | native |
| SS2 | SEQ ID NO: 10 | GIVRKWISRFEVWPYLKK | active |
| SS11 | SEQ ID NO: 11 | ILRVPFRTENGIVRK (NH2) | inactive |
| SS12 | SEQ ID NO: 12 | GIVRKWISRFEVWPYL (NH2) | active |
| SS15 | SEQ ID NO: 13 | GIVRKAISRFEVAPYL (NH2) | less active |
| SS16 | SEQ ID NO: 14 | SRFEVWPYL (NH2) | less active |
| SP3 | SEQ ID NO: 18 | RRISSVE DKK (NH2) | inactive |
| NR11 | SEQ ID NO: 15 | GPTLKRTASTAFMNTTSKK | inactive |
| SP26 | SEQ ID NO: 16 | GRMRRIATVEMMKK | inactive |
| SS1 | SEQ ID NO: 9 | GDRVLSRLHSVRERIGK | inactive |
| ACTIN | SEQ ID NO: 19 | EHGIVTNWDDMEKIWHHTFY | consensus |

Double basic cluster: black box; e.g. KK
Possible region of specificity: underlined or boxed
Substitutions: bold

Fig. 1B

| EN | GIVRK | WI | SRFEVW | PYL | KK |

$X_4$  $X_3$  $X_2$  $X_1$  $X_5$  $X_6$

| SEQ ID NO. | | SEQUENCE |
|---|---|---|
| SEQ ID NO:22 | $X_1$ | SRFEVW |
| SEQ ID NO:17 | $X_2$-$X_1$ | WISRFEVW |
| SEQ ID NO:14 | $X_1$-$X_5$ | SRFEVWPYL |
| SEQ ID NO:23 | $X_2$-$X_1$-$X_5$-$X_6$ | WISRFEVWPYLKK |
| SEQ ID NO:12 | $X_3$-$X_2$-$X_1$-$X_5$ | GIVRKWISRFEVWPYL |
| SEQ ID NO:10 | $X_3$-$X_2$-$X_1$-$X_5$-$X_6$ | GIVRKWISRFEVWPYLKK |
| SEQ ID NO:24 | $X_4$-$X_3$-$X_2$-$X_1$-$X_5$-$X_6$ | ENGIVRKWISRFEVWPYLKK |

A

B

Effect of SS2 on polymerized F-actin in vitro

SS2 bundling activity is not affected by phalloidin

SEQUENCE LISTING

```
<160> NUMBER OF SEQ ID NOS: 30

<210> SEQ ID NO 1
<211> LENGTH: 15
<212> TYPE: PRT
<213> ORGANISM: Artificial
<220> FEATURE:
<223> OTHER INFORMATION: synthetic consensus active Zea mays Sucrose
      Synthase (SuSy) peptide

<400> SEQUENCE: 1

Glu Asn Gly Ile Val Arg Lys Trp Ile Ser Arg Phe Glu Val Trp
1               5                   10                  15

<210> SEQ ID NO 2
<211> LENGTH: 15
<212> TYPE: PRT
<213> ORGANISM: Artificial
<220> FEATURE:
<223> OTHER INFORMATION: synthetic peptide derived from Zea mays SuSy1
      protein 367-381

<400> SEQUENCE: 2

Glu Asn Gly Ile Leu Arg Lys Trp Ile Ser Arg Phe Asp Val Trp
1               5                   10                  15

<210> SEQ ID NO 3
```

```
<211> LENGTH: 15
<212> TYPE: PRT
<213> ORGANISM: Artificial
<220> FEATURE:
<223> OTHER INFORMATION: synthetic peptide derived from Zea mays SuSy2
      protein 357-389

<400> SEQUENCE: 3

Glu Asn Gly Ile Val Arg Lys Trp Ile Ser Arg Phe Glu Val Trp
1               5                   10                  15

<210> SEQ ID NO 4
<211> LENGTH: 15
<212> TYPE: PRT
<213> ORGANISM: Artificial
<220> FEATURE:
<223> OTHER INFORMATION: synthetic peptide derived from Zea mays SuSy3
      protein

<400> SEQUENCE: 4

Glu Asn Gly Ile Leu Lys Lys Trp Ile Ser Arg Phe Asp Val Trp
1               5                   10                  15

<210> SEQ ID NO 5
<211> LENGTH: 15
<212> TYPE: PRT
<213> ORGANISM: Artificial
<220> FEATURE:
<223> OTHER INFORMATION: synthetic peptide derived from Drosophila
      melanogaster Actin 2 protein and Homo sapiens beta and gamma Actin
      proteins

<400> SEQUENCE: 5

Glu His Gly Ile Val Thr Asn Trp Asp Asp Met Glu Lys Ile Trp
1               5                   10                  15

<210> SEQ ID NO 6
<211> LENGTH: 15
<212> TYPE: PRT
<213> ORGANISM: Artificial
<220> FEATURE:
<223> OTHER INFORMATION: synthetic peptide derived from Drosophila
      melanogaster Actin 3, 5, and 6 proteins and Homo sapiens alpha
      Actin protein

<400> SEQUENCE: 6

Glu His Gly Ile Ile Thr Asn Trp Asp Asp Met Glu Lys Ile Trp
1               5                   10                  15

<210> SEQ ID NO 7
<211> LENGTH: 15
<212> TYPE: PRT
<213> ORGANISM: Artificial
<220> FEATURE:
<223> OTHER INFORMATION: synthetic peptide derived from Drosophila
      melanogaster ARP1

<400> SEQUENCE: 7

Glu His Gly Ile Val Lys Asp Trp Asn Asp Met Glu Arg Ile Trp
1               5                   10                  15

<210> SEQ ID NO 8
<211> LENGTH: 15
<212> TYPE: PRT
<213> ORGANISM: Artificial
<220> FEATURE:
<223> OTHER INFORMATION: synthetic peptide derived from Drosophila
      melanogaster ARP2

<400> SEQUENCE: 8
```

```
Glu Asn Gly Val Val Arg Asn Trp Asp Asp Met Cys His Val Trp
1               5                   10                  15

<210> SEQ ID NO 9
<211> LENGTH: 17
<212> TYPE: PRT
<213> ORGANISM: Artificial
<220> FEATURE:
<223> OTHER INFORMATION: synthetic SS1 inactive control peptide

<400> SEQUENCE: 9

Gly Asp Arg Val Leu Ser Arg Leu His Ser Val Arg Glu Arg Ile Gly
1               5                   10                  15

Lys

<210> SEQ ID NO 10
<211> LENGTH: 18
<212> TYPE: PRT
<213> ORGANISM: Artificial
<220> FEATURE:
<223> OTHER INFORMATION: SS2 active peptide based on Zea mays SuSy 377-
      392

<400> SEQUENCE: 10

Gly Ile Val Arg Lys Trp Ile Ser Arg Phe Glu Val Trp Pro Tyr Leu
1               5                   10                  15

Lys Lys

<210> SEQ ID NO 11
<211> LENGTH: 15
<212> TYPE: PRT
<213> ORGANISM: Artificial
<220> FEATURE:
<223> OTHER INFORMATION: SS11 inactive synthetic peptide

<400> SEQUENCE: 11

Ile Leu Arg Val Pro Phe Arg Thr Glu Asn Gly Ile Val Arg Lys
1               5                   10                  15

<210> SEQ ID NO 12
<211> LENGTH: 16
<212> TYPE: PRT
<213> ORGANISM: Artificial
<220> FEATURE:
<223> OTHER INFORMATION: SS12 active synthetic peptide

<400> SEQUENCE: 12

Gly Ile Val Arg Lys Trp Ile Ser Arg Phe Glu Val Trp Pro Tyr Leu
1               5                   10                  15

<210> SEQ ID NO 13
<211> LENGTH: 16
<212> TYPE: PRT
<213> ORGANISM: Artificial
<220> FEATURE:
<223> OTHER INFORMATION: SS15 less active synthetic peptide
<220> FEATURE:
<221> NAME/KEY: SITE
<222> LOCATION: (6)..(6)
<223> OTHER INFORMATION: replaced Tryptophan residue with Alanines
<220> FEATURE:
<221> NAME/KEY: SITE
<222> LOCATION: (13)..(13)
<223> OTHER INFORMATION: replaced Tryptophan residue with Alanine

<400> SEQUENCE: 13

Gly Ile Val Arg Lys Ala Ile Ser Arg Phe Glu Val Ala Pro Tyr Leu
```

-continued

```
1               5                  10                  15
```

<210> SEQ ID NO 14
<211> LENGTH: 9
<212> TYPE: PRT
<213> ORGANISM: Artificial
<220> FEATURE:
<223> OTHER INFORMATION: SS16 less active synthetic peptide
      corresponding to short middle portion of SS12 synthetic peptide

<400> SEQUENCE: 14

Ser Arg Phe Glu Val Trp Pro Tyr Leu
1               5

<210> SEQ ID NO 15
<211> LENGTH: 19
<212> TYPE: PRT
<213> ORGANISM: Artificial
<220> FEATURE:
<223> OTHER INFORMATION: NR11 inactive synthetic peptide

<400> SEQUENCE: 15

Gly Pro Thr Leu Lys Arg Thr Ala Ser Thr Ala Phe Met Asn Thr Thr
1               5                   10                  15

Ser Lys Lys

<210> SEQ ID NO 16
<211> LENGTH: 14
<212> TYPE: PRT
<213> ORGANISM: Artificial
<220> FEATURE:
<223> OTHER INFORMATION: SP26 inactive synthetic peptide

<400> SEQUENCE: 16

Gly Arg Met Arg Arg Ile Ala Thr Val Glu Met Met Lys Lys
1               5                   10

<210> SEQ ID NO 17
<211> LENGTH: 8
<212> TYPE: PRT
<213> ORGANISM: Artificial
<220> FEATURE:
<223> OTHER INFORMATION: Small block of SS12 sequence required for less
      active synthetic peptide

<400> SEQUENCE: 17

Trp Ile Ser Arg Phe Glu Val Trp
1               5

<210> SEQ ID NO 18
<211> LENGTH: 10
<212> TYPE: PRT
<213> ORGANISM: Artificial
<220> FEATURE:
<223> OTHER INFORMATION: SP3 inactive synthetic peptide

<400> SEQUENCE: 18

Arg Arg Ile Ser Ser Val Glu Asp Lys Lys
1               5                   10

<210> SEQ ID NO 19
<211> LENGTH: 20
<212> TYPE: PRT
<213> ORGANISM: Artificial
<220> FEATURE:
<223> OTHER INFORMATION: synthetic peptide of Drosophila melanogaster
      Actin protein consensus sequence
```

```
<400> SEQUENCE: 19

Glu His Gly Ile Val Thr Asn Trp Asp Asp Met Glu Lys Ile Trp His
1               5                   10                  15

His Thr Phe Tyr
            20

<210> SEQ ID NO 20
<211> LENGTH: 15
<212> TYPE: PRT
<213> ORGANISM: Artificial
<220> FEATURE:
<223> OTHER INFORMATION: synthetic peptide derived from Homo sapiens
      ARP1 protein

<400> SEQUENCE: 20

Glu His Gly Val Val Arg Asp Trp Asn Asp Met Glu Arg Ile Trp
1               5                   10                  15

<210> SEQ ID NO 21
<211> LENGTH: 15
<212> TYPE: PRT
<213> ORGANISM: Artificial
<220> FEATURE:
<223> OTHER INFORMATION: synthetic peptide derived from Homo sapiens
      ARP2 protein

<400> SEQUENCE: 21

Glu Asn Gly Ile Val Arg Asn Trp Asp Asp Met Lys His Leu Trp
1               5                   10                  15

<210> SEQ ID NO 22
<211> LENGTH: 6
<212> TYPE: PRT
<213> ORGANISM: Artificial
<220> FEATURE:
<223> OTHER INFORMATION: Core minimum block of SS12 sequence required
      for less active synthetic peptide

<400> SEQUENCE: 22

Ser Arg Phe Glu Val Trp
1               5

<210> SEQ ID NO 23
<211> LENGTH: 13
<212> TYPE: PRT
<213> ORGANISM: Artificial
<220> FEATURE:
<223> OTHER INFORMATION: SS synthetic peptide B

<400> SEQUENCE: 23

Trp Ile Ser Arg Phe Glu Val Trp Pro Tyr Leu Lys Lys
1               5                   10

<210> SEQ ID NO 24
<211> LENGTH: 20
<212> TYPE: PRT
<213> ORGANISM: Artificial
<220> FEATURE:
<223> OTHER INFORMATION: SS synthetic peptide C

<400> SEQUENCE: 24

Glu Asn Gly Ile Val Arg Lys Trp Ile Ser Arg Phe Glu Val Trp Pro
1               5                   10                  15

Tyr Leu Lys Lys
            20
```

```
<210> SEQ ID NO 25
<211> LENGTH: 20
<212> TYPE: PRT
<213> ORGANISM: Artificial sequence
<220> FEATURE:
<223> OTHER INFORMATION: Consensus sequence of Synthetic Susy and ARP
      sequences
<220> FEATURE:
<221> NAME/KEY: VARIANT
<222> LOCATION: (2)..(2)
<223> OTHER INFORMATION: X=His or Asn
<220> FEATURE:
<221> NAME/KEY: VARIANT
<222> LOCATION: (5)..(5)
<223> OTHER INFORMATION: X= Val or Leu or Ile
<220> FEATURE:
<221> NAME/KEY: VARIANT
<222> LOCATION: (6)..(6)
<223> OTHER INFORMATION: X= Arg or Thr or Lys
<220> FEATURE:
<221> NAME/KEY: VARIANT
<222> LOCATION: (7)..(7)
<223> OTHER INFORMATION: X= Lys, Asn, Asp
<220> FEATURE:
<221> NAME/KEY: VARIANT
<222> LOCATION: (9)..(9)
<223> OTHER INFORMATION: X= Ile or Asp or Asn
<220> FEATURE:
<221> NAME/KEY: VARIANT
<222> LOCATION: (10)..(10)
<223> OTHER INFORMATION: X= Ser or Asp
<220> FEATURE:
<221> NAME/KEY: VARIANT
<222> LOCATION: (11)..(11)
<223> OTHER INFORMATION: X= Arg or Met
<220> FEATURE:
<221> NAME/KEY: VARIANT
<222> LOCATION: (12)..(12)
<223> OTHER INFORMATION: X= Glu, Phe, Cys, or Lys
<220> FEATURE:
<221> NAME/KEY: VARIANT
<222> LOCATION: (13)..(13)
<223> OTHER INFORMATION: X= Glu, Asp, Lys, Arg, or His
<220> FEATURE:
<221> NAME/KEY: VARIANT
<222> LOCATION: (14)..(14)
<223> OTHER INFORMATION: X= Ile, Leu, or Val
<220> FEATURE:
<221> NAME/KEY: VARIANT
<222> LOCATION: (16)..(16)
<223> OTHER INFORMATION: X= His or none
<220> FEATURE:
<221> NAME/KEY: VARIANT
<222> LOCATION: (17)..(17)
<223> OTHER INFORMATION: X= His or none
<220> FEATURE:
<221> NAME/KEY: VARIANT
<222> LOCATION: (18)..(18)
<223> OTHER INFORMATION: X= Thr or none
<220> FEATURE:
<221> NAME/KEY: VARIANT
<222> LOCATION: (19)..(19)
<223> OTHER INFORMATION: X= Phe or none
<220> FEATURE:
<221> NAME/KEY: VARIANT
<222> LOCATION: (20)..(20)
<223> OTHER INFORMATION: X= Tyr or none

<400> SEQUENCE: 25

Glu Xaa Gly Ile Xaa Xaa Xaa Trp Xaa Xaa Xaa Xaa Xaa Xaa Trp Xaa
1               5                   10                  15

Xaa Xaa Xaa Xaa
            20

<210> SEQ ID NO 26
<211> LENGTH: 15
<212> TYPE: PRT
```

<213> ORGANISM: Artificial sequence
<220> FEATURE:
<223> OTHER INFORMATION: Motif for a synthetic peptide which causes
      actin bundling and inhbits actin depolymerization
<220> FEATURE:
<221> NAME/KEY: VARIANT
<222> LOCATION: (2)..(2)
<223> OTHER INFORMATION: X = any amino acid
<220> FEATURE:
<221> NAME/KEY: VARIANT
<222> LOCATION: (4)..(4)
<223> OTHER INFORMATION: X = Ile or Val
<220> FEATURE:
<221> NAME/KEY: VARIANT
<222> LOCATION: (5)..(7)
<223> OTHER INFORMATION: X = any amino acid
<220> FEATURE:
<221> NAME/KEY: VARIANT
<222> LOCATION: (9)..(14)
<223> OTHER INFORMATION: X = any amino acid

<400> SEQUENCE: 26

Glu Xaa Gly Xaa Xaa Xaa Xaa Trp Xaa Xaa Xaa Xaa Xaa Xaa Trp
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Motif for a synthetic peptide that causes actin
      bundling and inhibits actin depolymerization
<220> FEATURE:
<221> NAME/KEY: VARIANT
<222> LOCATION: (2)..(2)
<223> OTHER INFORMATION: X= Lys, Arg, or His
<220> FEATURE:
<221> NAME/KEY: VARIANT
<222> LOCATION: (5)..(5)
<223> OTHER INFORMATION: X= Ala, Val, Leu, Ile, Phe, Trp, Pro, or Met
<220> FEATURE:
<221> NAME/KEY: VARIANT
<222> LOCATION: (6)..(6)
<223> OTHER INFORMATION: X= Lys, Arg, or His
<220> FEATURE:
<221> NAME/KEY: VARIANT
<222> LOCATION: (7)..(7)
<223> OTHER INFORMATION: X= any amino acid
<220> FEATURE:
<221> NAME/KEY: VARIANT
<222> LOCATION: (9)..(13)
<223> OTHER INFORMATION: X= any amino acid
<220> FEATURE:
<221> NAME/KEY: VARIANT
<222> LOCATION: (14)..(14)
<223> OTHER INFORMATION: X= Ala, Val, Leu, Ile, Phe, Trp, Pro, or Met

<400> SEQUENCE: 27

Glu Xaa Gly Ile Xaa Xaa Xaa Trp Xaa Xaa Xaa Xaa Xaa Xaa Trp
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Formula (I) for active synthetic peptides
<220> FEATURE:
<221> NAME/KEY: VARIANT
<222> LOCATION: (3)..(3)
<223> OTHER INFORMATION: X = Ile, Val, or Leu
<220> FEATURE:
<221> NAME/KEY: VARIANT
<222> LOCATION: (4)..(4)
<223> OTHER INFORMATION: X = Arg, Lys, Asn, or Thr
<220> FEATURE:

```
<221> NAME/KEY: VARIANT
<222> LOCATION: (5)..(5)
<223> OTHER INFORMATION: X = Arg, Lys, Asn, or Asp
<220> FEATURE:
<221> NAME/KEY: VARIANT
<222> LOCATION: (7)..(7)
<223> OTHER INFORMATION: X = Ile, Asp, Asn, or Glu
<220> FEATURE:
<221> NAME/KEY: VARIANT
<222> LOCATION: (8)..(8)
<223> OTHER INFORMATION: X = Ser, or Asp
<220> FEATURE:
<221> NAME/KEY: VARIANT
<222> LOCATION: (9)..(9)
<223> OTHER INFORMATION: X = Arg, Met, or Ala
<220> FEATURE:
<221> NAME/KEY: VARIANT
<222> LOCATION: (10)..(10)
<223> OTHER INFORMATION: X = Phe, or Glu
<220> FEATURE:
<221> NAME/KEY: VARIANT
<222> LOCATION: (11)..(11)
<223> OTHER INFORMATION: X =Asp, Glu, Lys, Arg, or His
<220> FEATURE:
<221> NAME/KEY: VARIANT
<222> LOCATION: (12)..(12)
<223> OTHER INFORMATION: X =Val, or Ile
<220> FEATURE:
<221> NAME/KEY: VARIANT
<222> LOCATION: (14)..(14)
<223> OTHER INFORMATION: X =Pro, or His
<220> FEATURE:
<221> NAME/KEY: VARIANT
<222> LOCATION: (15)..(15)
<223> OTHER INFORMATION: X =Tyr, or His
<220> FEATURE:
<221> NAME/KEY: VARIANT
<222> LOCATION: (16)..(16)
<223> OTHER INFORMATION: X =Leu, or Thr

<400> SEQUENCE: 28

Gly Ile Xaa Xaa Xaa Trp Xaa Xaa Xaa Xaa Xaa Xaa Trp Xaa Xaa Xaa
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: Formula (II) for synthetic active peptides
<220> FEATURE:
<221> NAME/KEY: VARIANT
<222> LOCATION: (3)..(3)
<223> OTHER INFORMATION: X = Ala, Val, Leu, Ile, Phe, Trp, Pro, or Met
<220> FEATURE:
<221> NAME/KEY: VARIANT
<222> LOCATION: (4)..(4)
<223> OTHER INFORMATION: X = Lys, Arg, or His
<220> FEATURE:
<221> NAME/KEY: VARIANT
<222> LOCATION: (5)..(5)
<223> OTHER INFORMATION: X = any amino acid
<220> FEATURE:
<221> NAME/KEY: VARIANT
<222> LOCATION: (7)..(11)
<223> OTHER INFORMATION: X = any amino acid
<220> FEATURE:
<221> NAME/KEY: VARIANT
<222> LOCATION: (12)..(12)
<223> OTHER INFORMATION: X = Ala, Val, Leu, Ile, Phe, Trp, Pro, or Met

<400> SEQUENCE: 29

Gly Ile Xaa Xaa Xaa Trp Xaa Xaa Xaa Xaa Xaa Xaa Trp
1               5                   10

<210> SEQ ID NO 30
```

-continued

```
<211> LENGTH: 7
<212> TYPE: PRT
<213> ORGANISM: Artificial sequence
<220> FEATURE:
<223> OTHER INFORMATION: SS2 and SS12 subsequence necessary for peptide
      activity

<400> SEQUENCE: 30

Gly Ile Val Arg Trp Lys Ile
1               5
```

US 8,039,438 B2

SYNTHETIC PEPTIDES THAT CAUSE F-ACTIN BUNDLING AND BLOCK ACTIN DEPOLYMERIZATION

CROSS-REFERENCE TO RELATED APPLICATIONS

This application claims priority from U.S. Provisional Patent Application 60/513,275 filed on Oct. 20, 2003, which is incorporated by reference in its entirety.

STATEMENT OF GOVERNMENTAL SUPPORT

This invention was made during work supported by the U.S. Department of Energy under Contract Nos. DE-AC03-76SF00098 and DE-AI01-91ER20031 and the USDA-ARS under DOE Contract No. DE-AI05-91ER20031. The government has certain rights in this invention.

REFERENCE TO SEQUENCE LISTING

The attached paper copy of the Sequence Listing for this application is identical to the Sequence Listing in computer readable form found on the accompanying computer disk, as required by 37 CFR 1.821(c), both of which are hereby incorporated by reference in their entirety.

BACKGROUND OF THE INVENTION

1. Field of the Invention

This invention generally relates to the field of chemotherapeutic agents useful in the inhibition of cytokinesis and cell division for the research and treatment of cancers and other diseases.

2. Description of the Related Art

Highly regulated assembly and disassembly of actin monomers into filaments and bundles ("F-actin") is the essential basis for cell shape, cytokinesis and motility in eukaryotic cells. Actin filaments build a dynamic intracellular structure in all eukaryotic cells. These filaments as part of the cytoskeleton stabilize the cell and provide a network for unidirectional movement of proteins, which can mediate the localization of other proteins, mRNA or entire organelles. Actin binding proteins are involved in the organization of the actin filament network itself by crosslinking, capping or anchoring these microfilaments to membranes. The most abundant actin binding protein in a cell is actin itself. The actin monomer (ca. 43 kD) has four actin binding sites, which enables it to polymerize into filaments of different size and organization.

Polymerization of actin requires binding of ATP and subsequent hydrolysis into ADP and Pi. This exergonic reaction induces a conformational change in the monomer, exposing actin:actin binding sites. Only a few substances are known to modify the polymerization of actin. These compounds are useful tools to study the coordination and functions of the actin cytoskeleton in the cell.

Inhibiting cytoskeletal dynamics is one of the most powerful strategies employed in cancer treatment. Examples of compounds that bind to actin and inhibit cytoskeletal dynamics include such commonly used cancer drugs such as paclitaxel, eleutherobin, epithilone and discodermalide. However, drugs commonly used for this purpose cause serious side effects on fast-growing cells such as bone marrow cells, hair cells, intestinal brush border cells and germinmal cells, as degradation of these chemicals is slow. This problem is compounded by cumulative cytotoxicity on periferal organs.

The present invention relates to peptides derived by the inventors from sucrose synthase. Sucrose synthase (SuSy) is recognized as an important enzyme of sucrose (Suc) utilization in plant sink tissues. (L. C. Ho., *Annu. Rev. Plant Physiol. Plant Mol. Biol.* 39 (1988), pp. 355-378). In particular, the highest activity of SuSy often occurs during rapid growth (e.g. elongating maize leaves as described by B. Nguyen-Quoc, et al., Plant Physiol. 94 (1990), pp. 516-523) or during storage product deposition (e.g. developing seeds, as shown by S. S. Sung, et al., *Plant Cell Environ.* 17 (1994), pp. 419-426). SuSy is a globular protein and thus is generally considered to be soluble in the cytosol. However, some of the enzyme is known to be associated with the plasma membrane, perhaps in a specific complex with glucan synthase(s) in the membrane. Evidence that soluble SuSy binds to both G- and F-actin in vitro, as well as evidence that some of the SuSy may be associated with actin in situ is described in H. Winter, et al., *FEBS Letters*, Volume 430, Issue 3, 3 Jul. 1998, pages 205-208.

An alternative approach to the use of complex organic molecules to inhibit cell proliferation is the use of synthetic peptides. While other peptides have been shown to cause F-actin bundling in vitro, those peptides are generally highly basic in composition and promote formation of lateral aggregates of F-actin in a rather non-specific manner. In the long run, these compounds offer the prospect of minimalizing side effects by tumor cell-directed transfection of the sequences encoding the drug; in the short run, as peptides are inherently more easily degradable by the organism, they are not expected to cause cumulative cytotoxicity.

BRIEF SUMMARY OF THE INVENTION

The present invention comprises peptides loosely derived from the sequence of the *Zea mays* enzyme, Sucrose Synthase (SuSy), at amino acids 375-389 (Gen Bank Accession No. P49036). The present peptides share homology with many other sucrose synthases of other plant origin and with actin proteins and actin-related proteins from various organisms.

In one aspect of the invention, the application of active peptides of the invention result in stabilization of microfilaments and cause cross-linking of F-actin in vitro and in situ. The peptides of the present invention, along with inactive control peptides, may be characterized as follows, where the conventional single letter amino acid code letters are used and the derivative source of the peptide is indicated:

| | | |
|---|---|---|
| SEQ ID NO: 1 | ENGIVRKWISRFEVW | Consensus active SuSy peptide |
| SEQ ID NO: 2 | ENGILRKWISRFDVW | *Zea mays* SuSy1 367-381 |
| SEQ ID NO: 3 | ENGIVRKWISRFEVW | *Zea mays* SuSy2 375-389 |
| SEQ ID NO: 4 | ENGILKKWISRFDVW | *Zea mays* SuSy3 |
| SEQ ID NO: 5 | EHGIVTNWDDMEKIW | *Drosophila melanogaster* Actin 2; *Homo sapiens* β and γ Actin |
| SEQ ID NO: 6 | EHGIITNWDDMEKIW | *Drosophila melanogaster* Actin 3, 5, 6; *Homo sapiens* α Actin |

-continued

| SEQ ID NO: 7 | EHGIVKDWNDMERIW | Drosophila melanogaster ARP1 |
| SEQ ID NO. 8 | ENGVVRNWDDMCHVW | Drosophila melanogaster ARP2 |
| SEQ ID NO: 9 | GDRVLSRLHSVRERIGK | SS1 inactive Control peptide |
| SEQ ID NO: 10 | GIVRKWISRFEVWPYLKK | SS2 active peptide SuSy 377-392 |
| SEQ ID NO: 11 | ILRVPFRTENGIVRK | SS11 inactive peptide |
| SEQ ID NO: 12 | GIVRKWISRFEVWPYL | SS12 active synthetic peptide |
| SEQ ID NO: 13 | GIVRKAISRFEVAPYL | SS15 less active synthetic peptide |
| SEQ ID NO: 14 | SRFEVWPYL | SS16 less active synthetic peptide |
| SEQ ID NO: 15 | GPTLKRTASTAFMNTTSKK | NR11 inactive synthetic peptide |
| SEQ ID NO: 16 | GRMRRIATVEMMKK | SP26 inactive synthetic peptide |
| SEQ ID NO: 17 | WISRFEVW | SMIN less active synthetic peptide |
| SEQ ID NO: 18 | RRISSVEDKK | SP3 inactive synthetic peptide |
| SEQ ID NO: 19 | EHGIVTNWDDMEKIWHHTFY | Actin consensus sequence |
| SEQ ID NO: 20 | EHGVVRDWNDMERIW | Homo sapiens ARP1 |
| SEQ ID NO: 21 | ENGIVRNWDDMKHLW | Homo sapiens ARP2 |
| SEQ ID NO: 22 | SRFEVW | Core minimum SS synthetic peptide A |
| SEQ ID NO: 23 | WISRFEVWPYLKK | SS synthetic peptide B |
| SEQ ID NO: 24 | ENGIVRKWISRFEVWPYLKK | SS synthetic peptide C |

The invention also provides compounds comprised of consensus synthetic peptide sequences based upon native sequences such as sucrose synthase proteins, actin proteins or actin-related proteins, which share a common motif which may be provide for F-actin bundling and blocking actin depolymerization.

In one aspect, this activity may be conferred to such compounds by the presence of a shared motif described by the invention, and exemplified by the consensus sequence, Gly-Ile-$X_1$-$X_2$-$X_3$-Trp-$X_4$-$X_5$-$X_6$-$X_7$-$X_8$-$X_1$-Trp (SEQ ID NO: 29), where $X_1$ is a Val or other conservative substitution therefore, where $X_2$ is an Arg or other conservative substitution therefore, and $X_3$ to $X_8$ is any amino acid.

The invention provides for a peptide which comprises a subsequence: SRFEVW (SEQ ID NO: 22). The peptide comprises the formula: $X_4$-$X_3$-$X_2$-$X_1$-$X_5$-$X_6$, where $X_1$ is SREEVW, $X_2$ is WI, $X_3$ is GIVRK, $X_4$ is EN, $X_5$ is PYL, and $X_6$ is KK, wherein the peptide comprises $X_1$ and optionally at least one of $X_2$, $X_3$, $X_4$, $X_5$ and $X_6$, and if any of $X_2$, $X_3$, $X_4$, $X_5$ and $X_6$ are present the amino acids are identical in their respective positions to those in ENGIVRKWISRFEVW-PYLKK (SEQ ID NO: 24) as set forth in FIG. 1B. In one aspect, the peptide can be made up to 100 amino acids in length. The peptide can comprise the sequence of (SEQ ID NO: 17), (SEQ ID NO: 14), (SEQ ID NO: 23), (SEQ ID NO: 12), (SEQ ID NO: 10), or (SEQ ID NO: 24). In another aspect, the peptide is at least 80% homologous with a portion of native Zea mays protein sequence as set forth in GenBank Accession Number 1498382, and said homology is over the entire length of the peptide. In another aspect, the peptide causes 50% bundled actin and inhibits actin depolymerization when polymerized in vitro with actin. In another aspect, the amount of peptide needed to cause bundled actin and inhibit actin depolymerization is at least a molar ratio of peptide to actin of 100 to 1.

In another aspect of the invention, the peptides described cause cells to adopt a denser F-actin meshwork to form, whereby the organization of filamentous actin is changed. Upon addition of the peptides to normal fibroblast cells, the peptides block the depolymerization of F-actin, causing F-actin to adopt an abnormal spiky morphology. The peptides are also useful in blocking cell division resulting in a decreased number of cells after in vitro peptide treatment.

In another aspect, the peptides of the present invention can be used in cell culture or as a pharmaceutical drug to control diseases that involve uncontrolled cell division or neoplastic growth, such as cancer. The present peptides also provide a method for preventing migration of cells and can be used to prevent such migratory behavior as metastasis of cancer cells.

In another aspect, the present peptides also provide a method for blocking cell motility, in particular those behaviors and movements involved in "rocket-based motility." "Rocket-based motility" is the term used to describe the activity of such highly pathogenic bacteria such as Listeria which rely on actin cornet tails to provide the driving force for movement from cell to cell. The present peptides could be used as part of treatment to block motility and thus stop the spread of such bacteria.

In general, the present peptides as recited above will provide stabilization of microfilaments as measured by inhibition of actin depolymerization at concentrations of at least 0.1 mM up to 10 mM of peptide.

In another aspect, the invention provides for a method of inhibiting growth of cells, where the method comprises administering to the cells an amount of the peptide The invention further provides a method of treating a subject suffering from a disease characterized by cells having neoplastic growth, said method comprising a step of administering to the subject a therapeutically effective amount of the composition of claim 1. In one aspect the subject is a human and the peptide is administered at a dosage of 0.1 to 0.5 ml, one to five times per week.

The present peptides may be formulated according to known pharmaceutical technology. They may be administered singly or in combination, and may further be administered in combination with other cancer or actin-binding drugs. They may be conventionally prepared with excipients and stabilizers in sterilized, lyophilized powdered form for injection, or prepared with stabilizers and peptidase inhibitors of oral and gastrointestinal metabolism for oral administration. Alternatively, the peptides can be prepared with additives or fused to carrier molecules that would increase peptide efficacy and cell entry. Peptides containing naturally occurring amino acids may be produced intracellularly by introduction of DNA or RNA constructs.

BRIEF DESCRIPTION OF THE DRAWINGS

FIG. 1A is a listing of sequences discussed in the specification showing a sequence comparison of actin, sucrose synthase and the peptides of the invention. FIG. 1B shows a strategy for building active peptides from a core sequence.

FIGS. 5A and 5C are controls, FIGS. 5B and D show effects of addition of SS12.

DETAILED DESCRIPTION OF THE PREFERRED EMBODIMENT

Definitions

Figure 2:
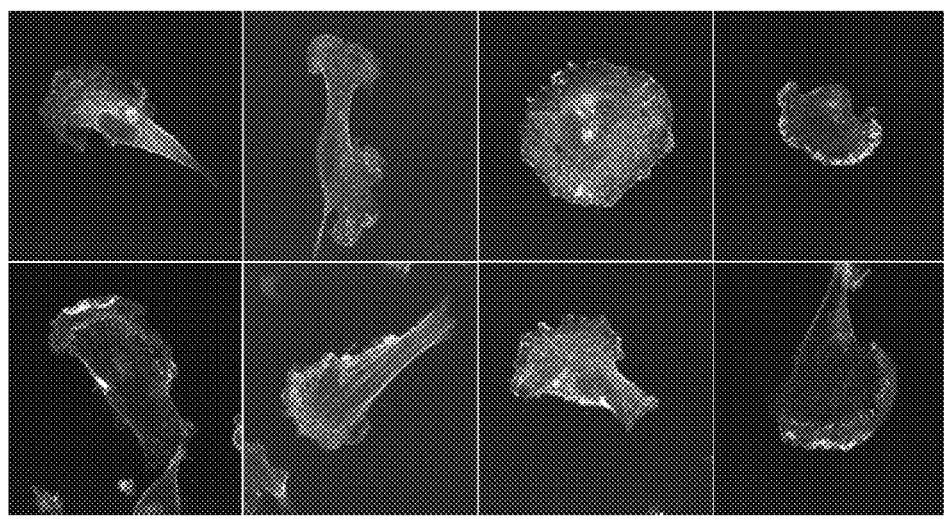
FIG. 2 is a series of microphotographs showing actin organization in human mammary epithelial tumor cells results in actin bundling to form long fillapodia extending from the cell surface (FIG. 2B) rather than the lamellipodia characteristic of crawling tumor cells (FIG. 2A).
Figure 2:
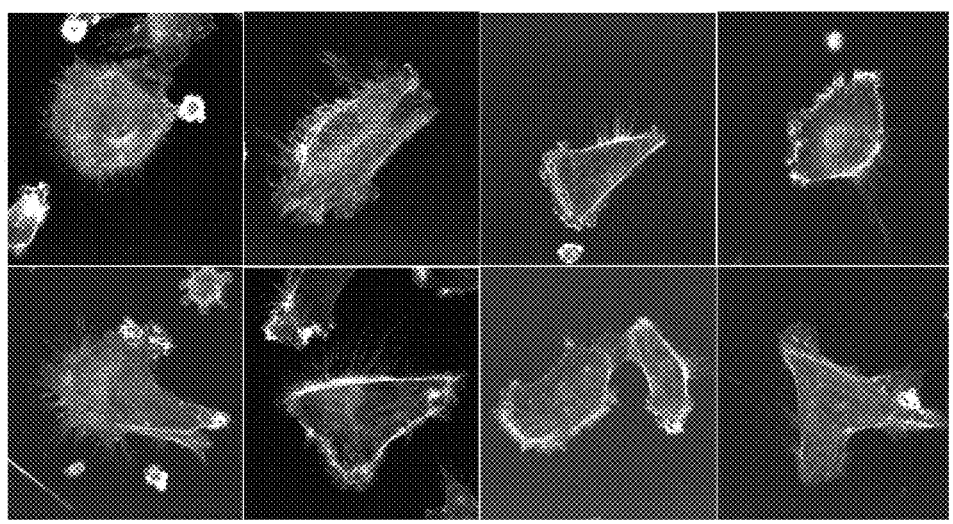

The term "peptide" herein refers to an amino acid sequence between 2 and 100 amino acids in length, the amino acids being joined by peptide linkages. The amino acids may be naturally and non-naturally occurring.

The terms "derived from" or "based on" herein refers to, regarding a peptide amino acid sequence, having a relationship to a native sequence of a plant-specific enzyme.

The term "substantially identical" is herein used to mean having an amino acid sequence which differs only by conservative amino acid substitutions or by non-conservative amino acid substitutions, deletions, or insertions located at positions which do not destroy the biological activity of the peptide. The term "homology" or "homologous" herein refers to an amino acid sequence similarity measured by the program, BLAST (Altschul et al (1997), "Gapped BLAST and PSI-BLAST: a new generation of protein database search programs", Nucleic Acids Res. 25:3389-3402 and expressed as –(% identity n/n). In measuring homology between a peptide and a protein of greater size, homology is measured only in the corresponding region; that is, the protein is regarded as only having the same general length as the peptide, allowing for gaps and insertions using default values. The term "substantially homologous" herein refers to a percent homology of at least 80%, more preferably 85%, even more preferably 90%, up to 91%, 92%, 93%, 94%, 95%, 96%, 97%, 98%, 99%, 99.5%, 99.8%, and 99.9% homology.

The term "cell" herein refers to human, other vertebrate, insect, bacterial, plant, yeast, or other unicellular organisms.

The term "motility" herein refers to cell behavior and movement. The term also refers to spontaneous and/or non-directional movement of cells—for examples, lamellipodial ruffling, crawling around the culture surface. Migration is a type of motility and cell migration and motility can be indicative of metastatic potential. The term "migration" herein refers to cell movement such as the crawling of cells from one tissue to another tissue, from tissue to blood stream to tissue, or (in the lab setting) from one side of a filter to the other. The term also describes directional migration and movement.

The term "metastatic potential" herein refers to the probability or potential spread of a disease from the organ or tissue of origin to another part of the body. The term also herein generally refers to the transmission of pathogenic microorganisms or cancerous cells from an original site to one or more sites elsewhere in the body, usually by way of the blood vessels or lymphatics.

The term "effective amount" herein refers to an amount sufficient to elicit the desired biological response.

The term "supra-additive" when used to refer to an effect from a combination of agents, herein refers to a total effect which is greater than the sum of the effects due to each of the individual agents.

The term "subject" herein refers to any vertebrate species. Particularly preferred subjects are mammals, with humans being the most preferred subject.

The term "conservative substitution" means a substitution where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. A non-conservative amino acid substitution is one where the residues do not fall into the same class, for example, substitution of a basic amino acid for a neutral or non-polar amino acid.

Introduction

Sucrose Synthase, an enzyme in higher plants with an important role in carbohydrate partitioning, was found to be associated with the actin cytoskeleton (Winter et al. *FEBS Lett.* 1998 Jul. 3; 430(3):205-8). In order to identify the actin binding site on Sucrose Synthase, a sequence of Sucrose Synthase with high homology to actin itself was identified. Synthetic peptides were derived from the consensus sequence, having similarity to the part of the actin sequence. The active peptides of the invention change the organization of the actin cytoskeleton of animal actin in vitro and in situ, possibly by binding specifically to one of the actin:actin binding sites. Thus, these peptides are not only useful as a powerful tool to study regulation of actin polymerization and function in cells, but also may be useful as chemotherapeutic agents. The active peptides of the invention also offer the prospects of tumor cell specific targeting, where the peptide may be synthesized intracellularly following transfection by a vector encoding the peptide. Such a vector may be designed using nucleic acid sequence encoding, e.g., peptide SS2, using the codons described.

Sequences and Sequence Analysis of Sucrose Synthase

Several actin binding proteins have been shown to display sequence and/or structural homology to segments of actin itself. See Tellam et al., *Trends Biochem Sci.* 1989 April; 14(4):130-3. In order to polymerize into double helical filamentous structures, each actin monomer must bind to four adjacent actin monomers, which led to the assumption that each actin monomer must have at least 4 different actin binding sites conformationally active upon binding and hydrolysis of ATP. It was therefore postulated that this pattern bf sequence similarity between actin and actin binding proteins reflects the molecular mimicry by these actin filament capping/severing proteins of a site on actin involved in actin-actin interactions (Tellam et al. *Trends Biochem Sci.* 1989 April; 14(4):130-3; Puius et al., *Curr Opin Cell Biol.* 1998 February; 10(1):23-34). Classes of actin capping, severing or crosslinking proteins share homology with segments of the actin structure itself and in some cases these sequences have been shown to be involved in the association of those proteins with monomeric or filamenteous actin (See Tellam et al. 1989).

The sequence homology of SuSy, actin related proteins (ARPs), actin and the specific activity of the synthetic peptides on the organization of actin filaments in vitro and in situ suggests a specific binding site of SuSy and ARPs shared with actin itself on the lateral site of actin filaments. In order to regulate the assembly of actin or the motility based on actin filaments or polymerization, association of the proteins to actin are regulated by affinity, posttranslational modification or effectors. While interaction with other proteins (i.e. ActA) might be a regulatory factor between capping, nucleating and branching activity of the ARP2/3 protein, binding of SuSy to actin is metabolically induced by high concentrations of its substrate sucrose or maltose.

In order to identify the actin binding site on SuSy, a sequence similarity analysis with BLAST (Altschul et al. 1997) was carried out and the SuSy sequence was compared with known actin binding sites from other proteins. A database search revealed a high homology between the following sequences: sequences of SUS1 and SUS2, SS2 (SEQ ID NO: 10), actin itself and actin-related proteins in other organisms as described in Example 1 and shown in Table 1.

Table 1 below shows the sequence alignment between 18 residue homologous sequences of three isoforms of SuSy isolated from *Zea mays* and with actin and actin-related proteins (ARP) found in *Drosophila melanogaster* (Dro me) and humans (*Homo sapiens*).

TABLE 1

| SEQ ID NO | Protein | Species | Position | Sequence |
|---|---|---|---|---|
| SEQ ID NO:1 | SuSy consensus | Zea mays | | ENGIVRKWISRFEVW |
| SEQ ID NO:2 | SuSy 1 | Zea mays | 367-381 | ENGILRKWISRFDVW |
| SEQ ID NO:3 | SuSy 2 | Zea mays | 375-389 | ENGIVRKWISRFEVW |
| SEQ ID NO:4 | SuSy 3 | Zea mays | | ENGILKKWISRFDVW |
| SEQ ID NO:5 | Actin 2; β γ Actin | Dro me; H. sapiens | 73-87; 72-86 | EHGIVTNWDDMEKIW |
| SEQ ID NO:6 | Actin 3, 5, 6; α Actin | Dro me; H. sapiens | 73-87; 74-88 | EHGIITNWDDMEKIW |
| SEQ ID NO:19 | Actin consensus | | | EHGIVTNWDDMEKIWHHTFY |
| SEQ ID NO:7 | ARP1 | Dro me | 76-90 | EHGIVKDWNDMERIW |
| SEQ ID NO:8 | ARP2 | Dro me | 75-89 | ENGVVRNWDDMCHVW |
| SEQ ID NO:20 | ARP1 | H. sapiens | 76-90 | EHGVVRDWNDMERIW |
| SEQ ID NO:21 | ARP2 | H. sapiens | 80-94 | ENGIVRNWDDMKHLW |
| | | | CONSENSUS | E+GI++-W-----+W--- |

The *Drosophila* sequence (SEQ ID NO: 5) is identical to human beta and gamma actin. Human alpha actin has one exchanged residue which makes it identical to *Drosophila* actin 3, 5, 6 (SEQ ID NO: 6). There are two human actin-related (ARP) proteins (SEQ ID NO: 20 and 21) with a similar sequence to Drosophila ARP1 and ARP2 (SEQ ID NO: 7 and 8), which are important for filapodia formation and cell division. In a GenBank BLAST search, the Actin consensus sequence, SEQ ID NO; 19, is found in actin proteins conserved across various organisms including *Saccharomyces cerevisiae* to *Drosophila melanogaster* to *Homo sapiens*.

The absolutely conserved residues across the organisms are indicated and identified in the consensus peptide sequence. Using the numbering of SEQ ID NO: 1, the absolutely conserved residues are E1, G3, I4, W8 and W15, with the exception of SEQ ID NO: 8 in which I4 is V4. Highly conserved amino acid substitutions are marked with a plus sign (+) in the consensus sequence. The dashed lines (-) in the consensus sequence indicate that the residues in that position are not highly conserved across organisms Actin-Blocking Peptides Sucrose synthases, actins, actin-like and actin-related proteins were aligned to find the consensus sequence shown in Table 1. Based upon the consensus sequence, different peptides can be created to determine their actin-blocking ability.

Thus peptides can be made, having the sequence of E-GI*---W------W, (SEQ ID NO:26) where, I* means I or V, "-" means any amino acid, wherein the peptide causes actin bundling and inhibits actin depolymerization when polymerized in vitro with actin. In another embodiment, a peptide can be made having the sequence, EH*GIV*R*-W-----V*W (SEQ ID NO: 27), where H* means H or a conservative substitution therefore, V* means V or a conservative substitution therefore, and R* means R or a conservative substitution therefore, and means any amino acid, wherein said peptide causes actin bundling and inhibits actin depolymerization when polymerized in vitro with actin.

Short synthetic peptides, as used in this study, usually display random conformation in aqueous solutions. The specific effects of the synthetic peptides on actin polymerization in vitro and in situ indicate that the sequence of amino acids in this peptide either determine a specific secondary structure or are active independent of the conformation. Formation of actin bundles can be caused in vitro by a number of polycations and basic polypeptides, largely independent of the specific structure of the bundling agent used (Tang and Janmey, *J Biol Chem.* 1996 Apr. 12; 271(15):8556-63).

This motif, exemplified by the consensus sequence of Table 1, has not been identified by analysis of crystal structures of actin, side-directed mutagenesis, mutant analysis in yeast or high-resolution electron micrographs, as being involved in the association of actin monomers to build filaments or bundles. The motif is not found in any other known actin binding proteins in searches using available programs such as ProSite and BLAST. Therefore this site seems to be unique to actin, ARPs and SuSy.

Referring now to FIG. 1, the underlined portion of sequence in SUS1, SUS2, SS2, SS11, SS12, SS15 and the actin consensus sequence, and the sequence shown within the box indicate possible regions of specificity. As shown in the examples below, both the underlined portion of sequence and the boxed regions of specificity appear to be necessary for actin-bundling activity.

Also shown, in black boxed with reversed out-type, are double basic residue clusters. Clusters of basic amino acids in synthetic peptides have been shown to affect actin polymerization (Tang and Janmey, *J Biol Chem.* 1996 Apr. 12; 271 (15):8556-63). The possibility of a charge-related effect with a synthetic peptide containing two "double-basic clusters" (SP26) was tested. This peptide was not able to bundle actin filaments in vitro. Peptides, such as SS11 and SP26 (FIG. 1), containing "basic clusters" similar to the motif were not effective in bundling, while the addition of basic residues, such as in SS2 (FIG. 1), did not increase the bundling activity, thus demonstrating that the double basic clusters are not the sole region responsible for actin bundling, but may contribute.

The specificity of the consensus sequence was further narrowed down by varying the synthetic peptides at the N-terminal (SS11) and C-terminal (SS16) portion of the peptide and then co-polymerizing the peptides with actin in vitro (see Table 2 and FIG. 6A-F for bundling activities).

Combining the above information, it appears that all amino acid residues which are identical or conserved between SuSy, and ARPs and Actin sequences of various organisms (Table 1) are essential for bundling at high affinity. Based on this observation, peptides exhibiting the motif in the consensus sequence of Table 1 should have actin bundling activity and the ability to block actin depolymerization.

In one embodiment, such peptides are created substantially homologous to the consensus sequence of Table 1. Effective peptides made using this formula should cause in vitro F-actin bundling and block acting depolymerization at peptide to actin ratios at least 100:1, more preferably 50:1, even more preferably about 20:1, more preferably 10:1, and most preferably at least 1:1. As shown in later examples, the first two residues in the Table consensus sequence may not be fully necessary for full activity. Therefore, in another embodiment, the peptides are created substantially homologous to a consensus sequence having the formula of formula (II):

Gly-Ile-$X_1$-$X_2$-$X_3$-Trp-$X_4$-$X_5$-$X_6$-$X_7$-$X_8$-$X_1$-Trp (SEQ ID NO:29), where $X_1$ is Val or a conservative substitution therefore, $X_2$ is Arg or a conservative substitution therefore, and $X_3$ to $X_8$ can be any amino acid.

In another embodiment, active peptides can be fashioned using the formula (I) comprising: Gly-Ile-$X_1$-$X_2$-$X_3$-Trp-$X_4$-$X_5$-$X_6$-$X_7$-$X_8$-$X_9$-Trp-$X_{10}$-$X_{11}$-$X_{12}$ (SEQ ID NO:28) or a pharmaceutically acceptable salt thereof. In a preferred embodiment, the addition of a compound of formula (I) results in about 50% of bundled actin when polymerized in vitro with actin. In such an embodiment, each residue of the formula may be as follows:

$X_1$=Ile, Val, or Leu
$X_2$=Arg, Lys, Asn, or Thr
$X_3$=Arg, Lys, Asn, or Asp
$X_4$=Ile, Asp, Asn, or Glu
$X_5$=Ser, or Asp
$X_6$=Arg, Met, or Ala
$X_7$=Phe, or Glu
$X_8$=Asp, Glu, Lys, Arg, or His
$X_9$=Val, or Ile
$X_{10}$=Pro, or His
$X_{11}$=Tyr, or His
$X_{12}$=Leu, or Thr

In a preferred embodiment, active peptides are made, wherein the peptides are substantially identical to the consensus sucrose synthase sequence SEQ ID NO: 1.

Based upon the consensus sucrose synthase sequence SEQ ID NO: 1, different synthetic peptides were created that possess actin-binding properties similar to SuSy and actin-related proteins and having the function of blocking actin depolymerization and F-actin bundling. Table 2 shows synthetic peptides that were made based on the consensus sucrose synthase protein in SEQ ID NO: 1. Table 2 shows the different peptides made and aligns them relative to the Control SS1 peptide. In a preferred embodiment, the sequence of the active synthetic peptides is substantially homologous to the active synthetic peptides, SEQ ID NOS: 10 and 12.

TABLE 2

| SEQ ID NO. | synthetic peptide | Sequence | In vitro actin bundling activity |
|---|---|---|---|
| SEQ ID NO:9 | SS1 | GDRVSRLIHSVRERIGK | CONTROL |
| SEQ ID NO:10 | SS2 | GIVRKWISRFEVWPYLKK | active |
| SEQ ID NO:11 | SS11 | ILRVPFRTENGIVRK | inactive |
| SEQ ID NO:12 | SS12 | GIVRKWISRFEVWPYL | active |
| SEQ ID NO:13 | SS15 | GIVRKAISRFEVAPYL | less active |

TABLE 2-continued

| SEQ ID NO. | synthetic peptide | Sequence | In vitro actin bundling activity |
|---|---|---|---|
| SEQ ID NO:14 | SS16 | SRFEVWPYL | less active |
| SEQ ID NO:15 | NR11 | GPTLKRTASTAFMNTTSKK | inactive |
| SEQ ID NO:16 | SP26 | GRMRRIATVEMMKK | inactive |
| SEQ ID NO:17 | SMIN | WISRFEVW | less active |
| SEQ ID NO:18 | SP3 | RRISSVEDKK | inactive |

While the synthetic peptide of tile N-terminal sequence (SS11) did not cause actin to bundle during in vitro polymerization, the C-terminal segment alone (SS16) bundled actin, but with reduced affinity. A similar effect was observed with a synthetic peptide where the two conserved tryptophans were substituted by alanine (alanine substitutions are shown in bold type in SS15). The alignment in Table 2 further demonstrates that certain residues in the Table 1 consensus sequence such as the tryptophans, W8 and W15, may be necessary for active peptides, as shown by SEQ ID NO: 17, Table 2.

Thus the invention further provides for a strategy of building active peptides based upon core sequences having minimal actin bundling activity. Active peptides can be made from discrete blocks of sequence from native sucrose synthase proteins, actin proteins or actin-related proteins, wherein the core blocks of sequence have substantial homology to the consensus sequence of Table 1. In such embodiments, if extended beyond the core sequence, the peptide can be extended using the corresponding amino acid sequence of a native sequence such as the *Zea mays* sucrose synthase protein or a human actin protein or actin-related protein. For example, based on the in vitro bundling activities of SEQ ID NO: 14 and SEQ ID NO: 17, SEQ ID NO: 22 can be seen as the basic core peptide from which a fully active synthetic peptide can built upon, in order to create an active peptide such as SEQ ID NO: 10 or 12. Such a strategy of slowly building peptides from smaller core blocks of sequence may be useful in cases where a smaller peptide is required, but the actin bundling activity must be retained.

FIG. 1B shows an example of a strategy of building active peptides based upon core sequences having minimal actin bundling activity. Table 3 shows the peptides that can be generated from various permutations, wherein each block of sequence is added sequentially or non-sequentially to generate an extended peptide.

In this example, an active peptide, $X_1$, can be a first sequence of SEQ ID NO: 22 as the minimal block of sequence for minimal activity. By building blocks of residues upon the core sequence, active peptides can be made. Using the final sequence shown, SEQ ID NO: 24, various smaller peptides can be made. In this example, $X_1$ is SEQ ID NO: 22, $X_2$ is Trp-Ile, $X_3$ is Gly-Ile-Val-Arg, $X_4$ is Glu-Asn, $X_5$ is Pro-Tyr-Leu, and $X_6$ is Lys-Lys. Thus, it is contemplated that sequences having any combination of the 6 sequence blocks can be made, so long as the core sequence $X_1$ is present Therefore, for examples, sequences that can be made, include, but are not limited to, $X_1$; $X_2$-$X_1$; $X_3$-$X_2$-$X_1$; $X_4$-$X_3$-$X_2$-$X_1$; $X_4$-$X_3$-$X_2$-$X_1$-$X_5$-$X_6$; $X_1$-$X_5$; $X_1$-$X_5$-$X_6$; $X_2$-$X_1$-$X_5$; $X_2$-$X_1$-$X_5$-$X_6$; $X_3$-$X_2$-$X_1$-$X_5$-$X_6$; $X_3$-$X_2$-$X_1$-$X_5$; and $X_4$-$X_3$-$X_2$-$X_1$-$X_5$.

It is contemplated that other peptides can be created using SEQ ID NO: 22, where non-sequential sequence blocks are added to SEQ ID NO: 22, however, the amino acids should be identical to their respective positions to those in ENGIVRK-WISRFEVWPYLKK (SEQ ID NO: 24) as set forth in FIG. 1B.

The peptides may be made and purified by methods known in the art, preferably by in vitro automated synthesis, but also by recombinant DNA methods. Furthermore, these peptides can be synthesized using D- or L-amino acids and selected non-natural or other modified amino acids, as is known in the art, in order to synthesize peptides which can act upon targets in the body and be degraded, yet do not interfere with normal protein function. The peptides can be stored in lyopholized form and dissolved in aqueous buffers or water prior to use. For the purposes of experimental use, the peptides are dissolved in sterilized degassed buffers to optimize biological activity to remain stable over 1-3 months at 4° C. Suitable buffers or diluents should be capable of solubilizing the active peptide, preferably below pH 8 to prevent the peptide from precipitating out of solution too easily.

TABLE 3

| SEQ ID NO. | synthetic peptide | Sequence | In vitro actin bundling activity |
|---|---|---|---|
| SEQ ID NO:22 | | SRFEVW | |
| SEQ ID NO:17 | SMIN | WISRFEVW | less active |
| SEQ ID NO:14 | SS16 | SRFEVWPYL | less active |
| SEQ ID NO:23 | | WISRFEVWPYL | |
| SEQ ID NO:12 | SS12 | GIVRKWISRFEVWPYL | active |
| SEQ ID NO:10 | SS2 | GIVRKWISRFEVWPYLKK | active |
| SEQ ID NO:24 | | ENGIVRKWISRFEVWPYLKK | |

In a preferred embodiment, synthetic peptides are made based on proteins and enzymes having actin binding capability and are substantially homologous to. SEQ ID NOS: 10 and 12 (SS2 and SS12 active peptides). It is further contemplated that the sequence are substantially identical to SEQ ID NOS: 10 and 12. Accordingly, they may be from about 13 to 100 amino acids in length, preferably 15-20 amino acids in length, more preferably 13-15 amino acids in length. The peptide subsequences can be extended in either the amino and carboxy direction or both, with the sequence from the native protein from which the peptide was derived.

When extending the peptides beyond the active synthetic peptide in the amino and/or carboxy directions, it is preferred that a native sequence from an actin or actin-related protein or sucrose synthase. In one embodiment, the sequence of the native *Zea mays* Sucrose Synthase 1, as set forth in GenBank Accession Number: P04712, native *Zea mays* Sucrose Synthase 2 and its isotypes, as set forth in GenBank Accession Number: P49036 and 2008300A, or the native sequence of the novel *Zea mays* Sucrose Synthase 3 at GenBank Accession Number: gi:22121990, may be used.

In another embodiment, the sequences of an actin protein from an organism, such as *Drosophila melanogaster*, is used to extend the peptide. For example, GenBank Accession Number: P10981 (Manseau, L. J., Ganetzky, B. and Craig, E. A, Molecular and genetic characterization of the Drosophila melanogaster 87E actin gene region, *Genetics* 119 (2), 407420 (1988)) or P53501 Fyrberg, E. A., Bond, B. J., Hershey, N. D., Mixter, K. S. and Davidson, N, The actin genes of Drosophila: protein coding regions are highly conserved but intron positions are not, *Cell* 24 (1), 107-116 (1981)) can be used. In another embodiment, the sequences of a native ARP2 protein from an organism, such as *Drosophila melanogaster*, is used to extend the peptide. For example, GenBank Accession Number: P02572 (Fyrberg, E. A., Bond, B. J., Hershey, N. D., Mixter, K. S. and Davidson, N, Direct Submission, December 1987) which discloses the sequence of an actin-related protein can be used.

In another embodiment, the human sequences of a native actin protein, such as human beta actin at GenBank Accession Number AAH16045.1 or human gamma actin at GenBank Accession Number JC5818. In another embodiment, the human sequences of a native actin-related protein, such as actin-related protein 2 isoform A (ARP2) at GenBank Accession Number NP_001005386.1, or actin-related protein 1 homolog B (ARP1) at GenBank Accession Number AAH06372.1.

The extended sequence need not be identical to the recited sequences above, however it should be substantially homologous, preferably at least 80% homologous, more preferably at least 90% homologous. Furthermore, the peptides having extended sequences should retain functionality of the synthetic peptides of F-actin bundling and blocking actin depolymerization.

It is further contemplated that the peptides are fused to a protein, signal sequence, peptide domain or other carrier molecule which would permit the entry of the SuSy peptides into mammalian cells. For example, the peptides can be made with the addition of Pep-1, a short amphipathic peptide carrier described in Morris, M C et al., *Nature Biotechnology* 19:1173-1176 (December 2001). Other methods of enhancing peptide delivery include but are not limited to, the linkage of competent signal peptides to the peptides, such as the NFκB sequence, described by Lin et al in U.S. Pat. No. 6,043,339 or the homeobox peptide, described by Fischer et al, in U.S. Pat. No. 6,472,507, covalently coupling the peptides to a nucleic acid-binding group, cationic lipids, dendrimers or other carrier molecules, or encapsulation or adsorption of the peptides of the invention in liposomes, microparticles, or nanoparticles.

The invention further contemplates the use of the peptides tagged with detectable agents including, but not limited to, antibodies, radioanalogs, products or compounds having distinctive absorption, fluorescence, or chemi-luminescence properties, such as rhodamine, fluorescein, green fluorescent protein (GFP) or semiconductor nanocrystal beads. Peptides tagged with such detectable agents would be useful for studying and monitoring the peptides and their effect on actin and microfilaments.

Application of the Active Peptides

The delivery of the preferred peptides of the invention into cells results in the stabilization of microfilaments and actin bundling.

The active peptides SS2 and SS12 of the preferred embodiment were shown to cause actin bundling, thereby preventing or decreasing cellular activities involving actin including cytokinesis, cell division, the ability to form lamellipodia, ruffling, motility and movement, cytoskeleton support and cell structure.

In one embodiment, the preferred peptides may result in the bundling of actin fibers by parallel binding. Referring to FIG. 2, upon the addition of the active peptides to normal fibroblast cells, the depolymerization of F-actin appears to have been blocked, causing F-actin to adopt an abnormal spiky morphology. FIG. 2 is a series of microphotographs showing actin organization in human mammary epithelial tumor cells results in actin bundling to form long fillapodia extending from the cell surface (FIG. 2B) rather than the lamellipodia characteristic of crawling tumor cells (FIG. 2A).

Figure 3:
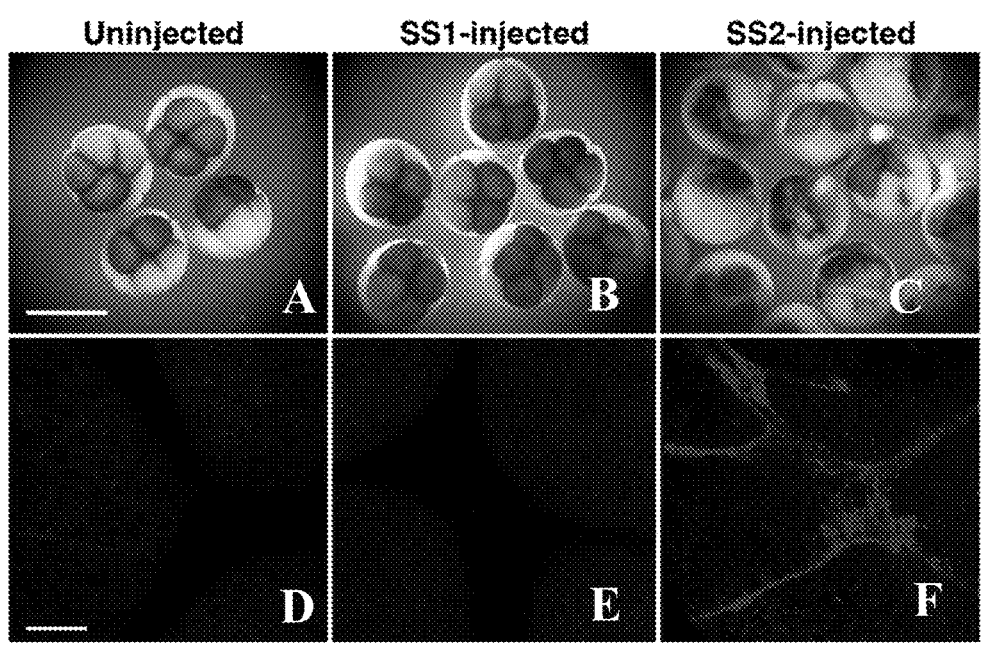
FIG. 3 is a series of color photographs of uninjected *Xenopus* blastomeres (FIG. 3A), upon injection of inactive peptides (FIG. 3B), and active peptide (FIG. 3C), and microphotographs of the blastomere cleavage furrows with actin stained with rhodamine-phalloidin in uninjected normal embryos (FIG. 3D), and in embryos injected with the inactive peptide (FIG. 3E) and with the active peptide (FIG. 3F).

In another embodiment, the peptides of the invention may also prove to be useful in blocking cell division as shown by FIG. 3. The injection of the active peptides of the invention to dividing cells will result in the inability to complete cell division through the stabilization of microfilaments. The peptides of the invention have a similar effect on actin as the compound, paclitaxel, which is widely used as an anti-tumor agent Therefore, the peptides of the invention will likely find use as anti-tumor agent.

Figure 4:
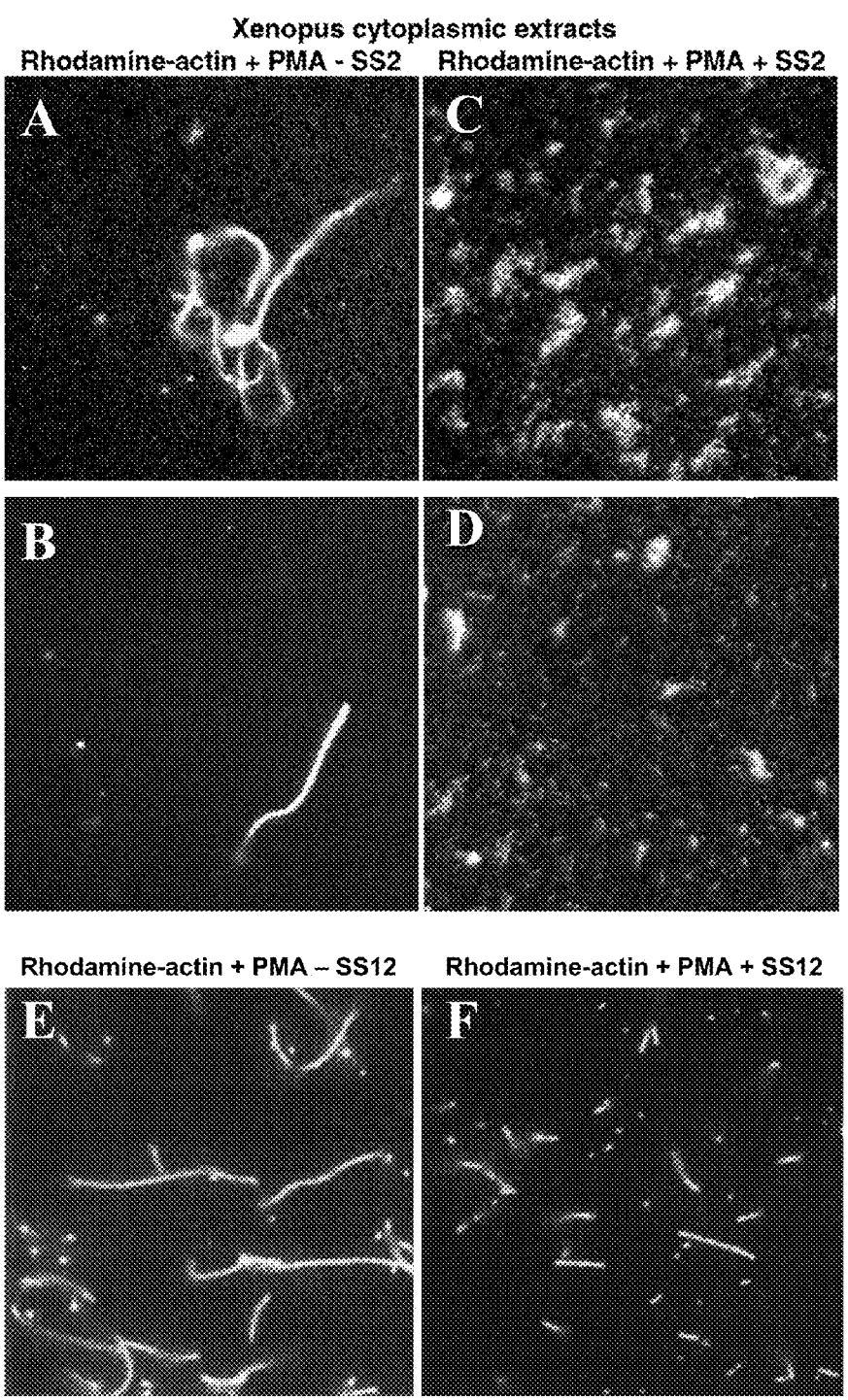
FIG. 4 is a series of six microphotographs of in Vitro polymerized actin comet tail formation. Rhodamine-labeled actin was added to cytoplasmic extracts shown in FIG. 4A. Addition of active peptides SS2 and SS12 caused complete disruption of the comet tails as shown in FIGS. 4C, 4D and 4F.

Referring to FIG. 4, in another embodiment, the present peptides also provide a method for blocking cell motility, in particular those behaviors and movements involved in "rocket-based motility." "Rocket-based motility" is the term used to describe the activity of such highly pathogenic bacteria such as *Listeria* which rely on actin comet tails to provide the driving force for movement from cell to cell. The present peptides could be used as part of treatment to block motility and thus stop the spread of such bacteria.

Figure 5:
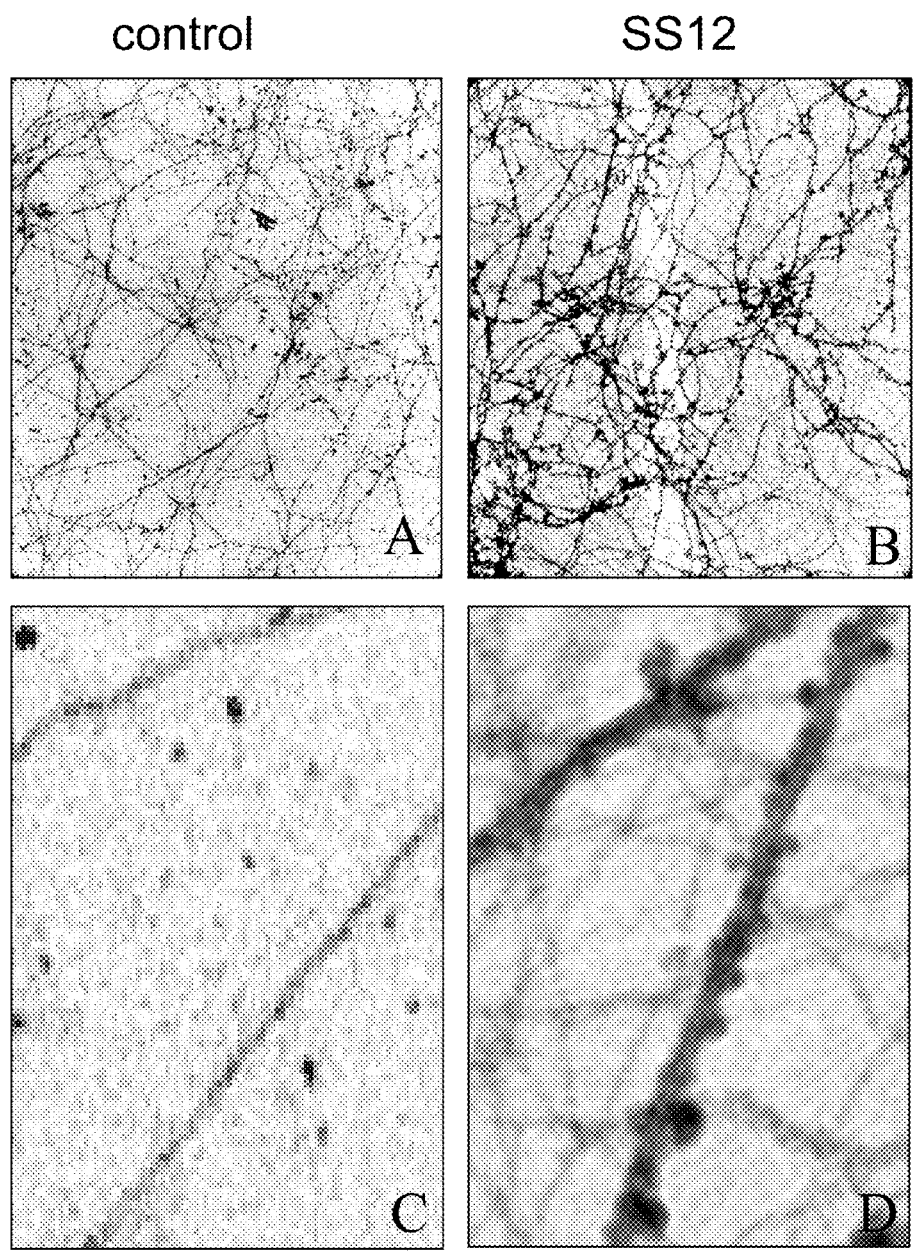
FIG. 5 is a series of electron micrographs of rabbit muscle actin bundled by co-polymerization with SS12 active peptide in a molar ratio of peptide:actin=2 showing the modulated shape of the filaments.

In another embodiment, the active peptides of the invention cause cells to form a denser F-actin meshwork, with the F-actin decorated as shown in FIG. 5. The addition of the active peptides to cells results in changing the organization of filamentous actin and increasing the amount of at least some proteins bound to actin in Vitro.

The present active peptides as recited above will provide stabilization of microfilaments and inhibition of in vitro actin depolymerization at a concentration of preferably at least 1:1 molar ratio of the peptide to actin, as demonstrated in the Examples and shown in FIG. 6A-6F. In a preferred embodiment, the peptides will result in approximately 100% stabilization of microfilaments in vitro at a 1:1 molar ratio of peptide to actin.

It will be apparent to those of skill in the art that the therapeutically effective amount of DNA or polypeptide of this invention will depend, inter alia, upon the administration schedule, the unit dose administered, whether the peptide or DNA is administered in combination with other therapeutic agents, the immune status and health of the patient, and the therapeutic activity of the peptide or DNA. The present peptides may be prepared according to known pharmaceutical methods. They may be administered singly or in combination, and may further be administered in combination with other chemotherapeutic drugs. The peptide can be conventionally prepared with a pharmaceutically acceptable additive, carrier, diluent, solvent, filler, lubricant, excipient, binder or stabilizer.

In a preferred embodiment, the peptides are administered by intratumoral injection at the situs of the cancer. One skilled in the art would understand and be able to use such methods of intratumoral injection of anti-tumor agents as disclosed by Flashner-Barak in U.S. Pat. No. 6,569,459 and hereby incorporated by reference. It is further contemplated that the peptides can be administered intravenously, systemically or orally in the form of a tablet, lozenge, capsule, powder, aqueous or oily suspension, syrup, elixir, implant or aqueous solution. In accordance with good clinical practice, it is preferred to administer the composition at a dose that will produce anticancer effects without causing undue harmful side effects.

The invention encompasses the delivery of the active peptides to tumors or regions of interest using various suitable delivery methods including, but not limited to, biodegradable microcapsules or immuno-stimulating complexes (IS-COMs), cochleates, polymers, microgels, slow-release molecules, or liposomes. The invention further contemplates the delivery of a polynucleotide encoding said active peptides having sequences obtained, e.g. by inputting peptide sequences into a reverse translation program such as "molecular tool kit" maintained by R. Bowen at Colorado State University. Such nucleic acids can be prepared using various suitable gene preparation and delivery methods including, but not limited to, genetically engineered attenuated live vectors such as viruses or bacteria, recombinant (chimeric) virus-like particles, e.g., bluetongue, or constructs and vectors containing the polynucleotide, and so-called "naked DNA."

The amount of adjuvant employed will depend on the type of adjuvant used. For example, when the mucosal adjuvant is cholera toxin, it is suitably used in an amount of 5 mg to 50 mg, for example, 10 mg to 35 mg. When used in the form of microcapsules, the amount used will depend on the amount employed in the matrix of the microcapsule to achieve the desired dosage. The determination of this amount is within the skill of a person of ordinary skill in the art.

The peptides of the invention are administered in amounts readily determined by persons of ordinary skill in the art. The following is meant to act as guidance. For adults a suitable dosage will likely be in the range of 10 mg to 10 g, preferably 10 mg to 100 mg, more preferably in the range of 5 mg to 500 mg. Similar dosage ranges will be applicable for children. Those skilled in the art will recognize that the optimal dose may be more or less depending upon the patient's body weight, disease, the route of administration, and other factors. Those skilled in the art will also recognize that appropriate dosage levels can be obtained based on results with known oral vaccines such as, for example, a vaccine based on an *E. coli* lysate (6 mg dose daily up to total of 540 mg) and with an enterotoxigenic *E. coli* purified antigen (4 doses of 1 mg) (Schulman et al., *J. Urol.* 150:917-921 (1993); Boedeker et al., *American Gastroenterological Assoc.* 999: A-22 (1993)). The number of doses will depend upon the disease, the formulation, and efficacy data from clinical trials. Without intending any limitation as to the course of treatment, it is contemplated that the treatment using the peptides can be administered over 3 to 8 doses for an administration schedule over 1 month (See Boedeker, *American Gastroenterological Assoc.* 888: A-222 (1993)).

While it is known that amino acid peptides tend to degrade quickly, the effects of the active peptides of the invention were found by the inventors to have effects on cell division as long as 36 hours upon administration of the peptide. In electroporation experiments, using cells having a 24 hr cell cycle division, within 36 hours there were decreased number of cells. Thus it is contemplated that subjects will be given an effective amount of the solution intratumorally, 0.1 to 0.5 ml, one to five times/week, using a syringe and a needle.

The following examples are provided as exemplary of the invention and should in no way be seen as limiting the invention to these specific examples.

Example 1

Sequence Analysis and Structural Comparison of Sucrose Synthase

Referring now to FIG. 1, use of BLASTP 2.0.8 revealed high homology between Sucrose Synthase sequence (SS2) with actin itself and actin-associating proteins. FIG. 1 shows that *Zea mays* Sucrose Synthase 2 (SUS2) residues 375-389 (SEQ ID NO: 3) have significant homology with *Zea mays* Sucrose Synthase 1 (SUS1) at residues 367-381 (SEQ ID NO: 2), with an expectancy score of 4e-04, 86% identical and 99% positively aligned. SUS2 has an expectancy score of 19, with 40% identity and 60% positives when aligned with residues 54-68 of *Zea mays* Actin (GenBank Accession No.: 1498382 (U60507)). FIG. 1 further shows a sequence similarity between the SUS1 and SUS2 sequences and a consensus sequence of various actin proteins. This indicates the presently recognized possibility of a binding site on actin for a peptide having sequence similarities in this region. Shown below the Actin consensus sequence are various synthetic peptides made according to the teachings of the present specification and the activity of those peptides. As discussed below, the most active peptides, SS2 and SS12 contained the underlined subsequence GIVRWKI (SEQ ID NO:30), which appears to be necessary, but not sufficient, for activity.

Example 2

Making Active Peptides

Using the consensus sequence in Table 1 which was derived from the aligned sequences of SuSy1, SuSy2, SuSy3 and actin, active synthetic peptides that bind and alter F-Actin polymerization were created. The dashed lines (-) represent unconserved amino acids, and the symbol (+) represents amino acids that are conservative substitutions. Table 2 shows different variations of the peptides made and their corresponding level of actin bundling. The peptides are soluble at lower pHs and preferably stored in low salt buffer (LSB: 5 mM Tris-HCl, pH 8.0, 0.2 mM $CaCl_2$, 0.2 mM ATP, 0.5 mM DTT).

The peptides were synthesized through commercial oligo-synthesis. Peptides were then lyophilized and resuspended in pH 8.0 buffer Tris-HCl at 1 mM concentration.

Example 3

Active Peptides Stabilize Microfilaments and Inhibit Cell Division

In this example, the active peptides were used to control cell division. The cells treated with the active peptide SS12

(SEQ ID NO: 12) showed a decrease in the number of cells after 24 hours compared to the cells treated with the inactive peptide. The cell division of the SS12 treated cells was inhibited for the 36 hours the cells were under observation.

Electroporated cells were treated with fluorescent dextran plus peptide so those cells receiving the peptide could be identified. Typically a very small number of cells successfully incorporate substance during electroporation, making it difficult to identify those receiving peptide. Typically one sees 10-20% incorporation. But, there is good evidence showing that if a cell incorporates one component in buffer, it will incorporate all components. Thus, dextran can be used to identify those cells receiving peptide. After electroporation of cells with fluorescent dextran and the active peptide SEQ ID NO: 12, the dextran-labeled cells were initially counted and then incubated for 18 hrs. After incubation overnight, the dextran-labeled cells were once again counted. The following Tables 4 and 5 show the average change in dextran-labeled cells after the cells are electroporated and the peptide has invaded the cell body. The cell numbers of the SS12 treated peptide seemed to fluctuate after incubation with various concentrations of the SS12 peptide. While there may be no actual decrease in the number of cells, in general it appears that the SS12 peptide treated cells did not exhibit the expected increase in cell population as observed with the SS1 (SEQ ID NO: 9) control peptide-treated cells.

TABLE 4

SS12 active peptide-electroporated cells, 6 dishes:

| Peptide Concentration | % change in cell number |
|---|---|
| 0.2 µM | +13.21 |
| 1.0 µM | −1.5 |
| 10.0 µM | −8.6 |
| 1.0 mM | +2.4 |
| 1.0 mM | −6.9 |
| 1.0 M | −12.5 |

TABLE 5

SS1 control-electroporated cells, 6 dishes:

| Peptide Concentration | % change in cell number |
|---|---|
| 0.2 µM | +1.2 |
| 1.0 µM | +17.4 |
| 10.0 µM | +43.8 |
| 1.0 mM | +64.9 |
| 1.0 mM | +38.4 |
| 1.0 M | +45.0 |

In further experiments, cytokinesis but not nuclear division was blocked in tumorogenic cells by addition of the active peptide SS12. MCF7 cells were electroporated with GFP-actin and imaged (image not shown). After addition of peptide in DMSO, the MCF7 cells were continuously imaged for up to 4 hours. The cells that incorporated the active peptide exhibited two nuclei but could not divide by cytokinesis. The actin filaments within the cells were observed by fluorescence and had the appearance of spikes. Thus it appears that treatment by the active peptide results in inhibition of cytokinesis and blocks cell division.

Example 4

Actin Reorganization After Peptide Treatment

Referring now to FIG. 2, it can be shown that treatment with an active peptide results in actin organization in human mammary epithelial tumor cells. MDA 231 cells were electroporated with SS1 (panel A) or SS12 (panel B), fixed, and rhodamine-phalloidin stained. Control epithelial tumor cells were treated with SS1 (SEQ ID NO: 9) resulting in no effect on actin-filled lamellipodia (or ruffling) characteristic of crawling cells. These normal cells treated with the inactive peptide are shown in FIG. 2A after treatment.

The MDA 231 cells treated with the peptide SS12 (SEQ ID NO: 12) are shown in FIG. 2B. MDA 231 cells are a particularly aggressive tumor cell line crawling and moving from between tissues. After treatment with the peptide, the cells no longer have lamellipodia; however they do exhibit numerous long spiky structures and fillopodial-like structures extending from the cell surface. Eventually, these cells ceased movement due to the bound F-actin.

Example 5

Effect of Peptides on Actin-Dependent Cleavage During Early Development

Referring now to photographs of FIG. 3 the peptides have a severely abnormal effect on the embryonic development of cells. Embryos from *Xenopus laevis* were injected with the inactive control peptide of SEQ ID NO: 9 and the active peptide of SEQ ID NO: 10. FIG. 3A shows normal, uninjected embryos at the 8-cell stage (only 4 blastomeres can be seen; the other 4 cells are directly beneath them.) The same concentration of the inactive peptide was injected into embryos and had no effect as shown in FIG. 3B. The embryos resemble the uninjected normal embryos of FIG. 3A FIG. 3C shows embryos that had been injected with 0.6 mg/mL (final concentration in egg) of the active peptide, SS2, and fixed at the same time period. When injected into the embryos, the SS2 peptide appeared to block several cell divisions, which typically are an hour apart. This demonstrates that the SS2 peptide does not degrade quickly but has a lasting effect on cell division for at least 3 divisions. The resulting blastomeres were unable to regain function and were severely abnormal showing abortive cleavage furrows.

The three bottom panels of FIG. 3 shows the effect of the active peptide on actin organization in embryos from *Xenopus laevis* as detected with rhodamine phalloidon, which labels filamentous actin. The uninjected normal embryos (FIG. 3D) and the embryos injected with the inactive peptide (FIG. 3E) successfully completed three divisions, forming 8-cell embryos with no residual filamentous actin seen between the blastomeres. However, in the embryos injected with the active peptide (FIG. 3F), filamentous actin is seen in the abortive cleavage furrows. Cleavage furrows had been initiated, suggesting actin bundling had occurred, but cytokinesis was blocked.

Thus, this example shows that administration of the active peptides should cause the bundling of F-actin in vivo, such as prohibiting the metastasis and growth characteristic of tumor cells.

Example 6

Effect of Peptides on Actin Comet-Tail Formation in Cytoplasmic Extracts

Referring now to FIG. 4, this example demonstrates that the present active peptides affect actin comet-tail formation in cytoplasmic extracts. In FIGS. 4A and 4B, in vitro polymerized actin forms comet tail from rhodamine-labeled actin added to *Xenopus laevis* egg cytoplasmic extract. This was set up according to the protocol in Taunton et al., *J Cell Biol.* 2000 Feb. 7; 148(3):519-30. The addition of the active peptide of SEQ ID NO: 3 (SuSy2) caused complete disruption of the comet tails as shown in FIGS. 4C and 4D.

As described by Taunton et al. in *J Cell Biol.* 2000 Feb. 7; 148(3):519-30, *Xenopus* Protein Kinase C (Chen et al. *Second Messengers Phosphoproteins*. (1998) 12:251-26), was cloned upstream of enhanced green fluorescent protein (GFP) (Heim et al., *Nature* 373:663-664, 1995), in the *Xenopus* expression vector CS2+. The resulting fusion protein, XPKC-GFP, is enzymatically active in vitro and in cultured cells is recruited to the plasma membrane in response to PMA, which is phorbol 12-myristate 13-acetate, a potent diacylglycerol mimetic that acts as an unspecific protein kinase activator (Sheldahl et al., *Curr. Biol.* 9:695-698 1999). PMA also plays a major role in the major cortical events of fertilization, including granule exocytosis, resumption of membrane trafficking, contraction of the cortex, and cleavage furrow formation (Bement and Capco, *J. Cell Biol.* 108:885-892 1989; Bement and Capco, *Proc. Natl. Acad Sci.* USA. 88:5172-5176, 1991).

Approximately 5 nl of XPKC-GFP RNA and 20 nl of a stock solution of rhodamine-labeled non-muscle actin (10 mg/ml in 2 mM Tris-HCl [pH 8.0], 0.2 mM $CaCl_2$, 0.2 mM ATP, and 0.5 mM DTT; Cytoskeleton) were injected into manually defolliculated stage VI oocytes. After 8-10 h, meiotic maturation was triggered by the addition of 1 µg/ml progesterone, and oocytes were incubated overnight in Barth's medium at 16-17° C. Several hours after germinal vesicle breakdown, oocytes were activated by pricking with a glass micropipet. Oocytes were mounted in viewing dishes for live cell analyses as described previously (Rowning et al., *Proc. Natl. Acad. Sci.* USA. 94:1224-1229, 1997; Larabell, *Methods Mol Biol*. 2000; 135:175-82, 1998), using a BioRad MRC 1024 confocal laser scanning microscope equipped with a Nikon Diaphot 200 microscope and a Nikon 60× PlanApo 1.4 NA oil immersion lens. XPKC-GFP constructs and rhodamine-actin were visualized using fluorescein and rhodaimine filters, respectively. Optical sections from the outer 20 µm were collected. For a given time-lapse sequence, multiple images of a single optical section were collected as rapidly as possible. Images were collected using a 512×512-pixel format at 1 frame per 3.5 sec for up to 1 hour. Data were analyzed using IMAGESPACE software (Molecular Dynamics, Piscataway, N.J.) on a Silicon Graphics computer.

Whole Mount Immunocytochemistry

Eggs were collected from adult frogs and fertilized as described previously by Rowning et al., *Proc. Natl. Acad. Sci.* USA. 94:1224-1229, 1997. Briefly, adult frogs (*Xenopus laevis*) were raised in the laboratory and fed trout chow (Purina) twice a week. Ovulation was induced by injecting 800 units of human chorionic gonadotropin (Sigma Chemicals, St. Louis, Mo.) into the dorsal lymph sac of each frog. Approximately 12 h later, eggs were stripped into a dry Petri dish and fertilized by overlaying them with a suspension of approximately one-eighth of a minced testis in 1-2 ml of one-third strength modified amphibian Ringer's solution (1/3 MR) (100% MR=100 mM NaCl, 2 mM KCl, 1 mM MgCl2, 2 mM CaCl2, 50 µg/ml gentamycin, and 5 mM Hepes adjusted to pH 7.2 with NaOH). Fertilization was allowed to proceed for 6-8 min before de-jellying eggs with 2.5% cysteine hydrochloride in 1/3 MR adjusted to pH 8.0 with NaOH. Eggs were then rinsed 3-5 times with fresh 1/3 MR. They were fixed overnight in 4% paraformaldehyde, 0.1% glutaraldehyde, 100 mM KCl, 3 mM $MgCl_2$, 10 mM HEPES, 150 mM sucrose, and 0.1% TRITON X-100 (pH 7.6). Nonspecific binding was blocked by incubation (1-2 h, with rotation) in 0.1% TRITON X-100 in Super Block (Pierce Biotechnology, Rock-ford, Ill.). Specimens were then incubated for 1 h with 0.16 µM fluorescein-phalloidin in Super Block. Eggs were viewed with a BioRad 1024 confocal laser scanning microscope using a fluorescein filter.

Cell-Free Reconstitution of Vesicle Movement

Crude *Xenopus* egg extract was prepared as described except that cytochalasin D was omitted (Murray and Kirschner, *Nature*. 1989 May 25; 339(6222):275-80). Cytosol and a heavy membrane fraction were prepared by centrifugation of the crude extract (2 h, 300.000 g max; BECKMAN SW-50 rotor). The viscous glycogen pellet beneath the membrane layer was discarded. Cytosol was further clarified by spinning for 15 min at 541,000 g max (BECKMAN TLA 100.3 rotor). Crude membranes (diluted with one volume of 2 M sucrose) and cytosol were snap frozen in separate aliquots for storage at −80° C. unless otherwise indicated. Clarified cytosol contained a small population of vesicles, but motility assays were far more robust (more comet tails over a longer time period) when cytosol was supplemented with the heavy membrane fraction.

For the standard assay, crude membranes in 1 M sucrose (20-µl aliquot, derived from ~80 µl crude extract) were washed and resuspended in 14 µl buffer A (50 mM NaCl, 5 mM $MgCl_2$, and 50 mM tris [pH 7.5]). To the membrane suspension were added 35 µl cytosol (derived from ~80 µl crude extract), 0.3 µl rhodamine-labeled actin (prepared according to Kellogg et al., *Development*. 1988 August; 103 (4):675-86), 3 µl PMA (20 µM stock in 10% DMSO), and 20 µl buffer A at 4° C. 20-µl samples were then warmed to room temperature. After 30-40 min, 2-µl aliquots were viewed with a Nikon E800 microscope to yield the photomicrographs of FIG. 4. Images were acquired with a Princeton Instruments cooled CCD camera (standard rhodamine filter set, Princeton Instruments, Trenton, N.J.) and analyzed with WINVIEW (Visitron System, Puchheim, Germany) or METAMORPH software (Princeton Instruments, Trenton, N.J.). Pixels having an intensity over a threshold value (set to a value greater than the background fluorescence in regions devoid of comet tails) were summed over 10 random fields to quantitate relative actin assembly.

Time-lapse sequences showing actin comet tails in *Xenopus* egg extracts are shown in FIG. 4. Cytosol was supplemented with a crude membrane fraction, rhodamine-actin, 1 µM PMA and peptide SS2 or SS12 (1 µM). After incubating at room temperature for 20 min, samples were viewed by fluorescence. Actin comet tails formed in *Xenopus* cytoplasmic extracts where no SS2 or SS12 peptides were added as shown by the photographs A, B and E of FIG. 4. In extracts where the SS2 or SS12 peptides were added, FIGS. 4 C, D and F, little or no actin comet tail formation was observed.

This example demonstrates that the active peptide can be used for blocking cell motility, in particular those behaviors and movements involved in "rocket-based motility." Highly pathogenic bacteria such as *Listeria* rely on actin comet tails to provide the driving force for movement from cell to cell. The SS12 peptide could be used as part of treatment to stop the spread of such bacteria.

Example 7

Actin Bundling and Decoration after Polymerization in Presence of SS12 Peptide

The actin bundles caused by co-polymerization of SS12 peptide with purified rabbit muscle actin in vitro were visualized by negative stain electron microscopy (FIG. 5). The bundles still show overall filamenteous structure about 3 times the width of actin filaments polymerized in vitro in the absence of SS12 peptide (FIG. 5A, B). The surface of the bundles is not smooth, but irregular, resembling attempts to branch or attachments of short actin bundles to the sides of the long ones (FIG. 5C). The peptide-bundled actin filaments are much shorter than the control filaments as visualized with rhodamine-phalloidin by fluorescence microscopy (data not shown).

Purified rabbit actin was polymerized in the presence or absence of the SS12 peptide and by absorption applied to a carbon coated copper grid. Negative contrastation was carried out with Pb-citrate and the dried grid was viewed in an Electron microscope at high magnifications (12,000× and 65,000×). As shown in FIG. 5, polymerization in the presence of the peptide SS12 showed an increased diameter of the actin microfilaments compared to the controls. Higher magnification identified a "modulated" decoration of the otherwise smooth filaments. The image of SS12-modified actin bundles suggests that the peptide mimicks an initiation of branching of the filaments.

Upon binding to ActA, the Arp2/3 complex has enhanced nucleating activity for actin polymerization (Skoble J, Portnoy D A, Welch M D, Three regions within ActA promote Arp2/3 complex-mediated actin nucleation and *Listeria monocytogenes* motility; *J Cell Biol.* 92000 Aug. 7; 150(3): 527-38). We tested a possible involvement of the homologous sequence on nucleating or capping activity by following the time-dependent fluorescence increase upon actin/pyrene-actin polymerization in the presence of the synthetic peptide SS12. SS12 did not show any nucleating or capping activity, but an increased fluorescence typical for an increased weight concentration of the pyrene-actin i.e. due to bundling of filaments (data not shown).

Example 8

In Vitro Bundling of Actin by Active Peptides

The peptides in Table 2 were added to polymerised actin in vitro at different molar ratios. Centrifugation was used to separate fractions containing F-actin, G-actin and bundled actin, which were then run out on agarose gels.

Purified rabbit muscle actin (Cytoskeleton Inc., Denver, Mo.) was depolymerized in Low Salt Buffer [LSB; 5 mM Tris-HCl, pH 8.0, 0.2 mM CaCl$_2$, 0.2 mM ATP, 0.5 mM DTT, mM sucrose) for 1 h on ice and denucleated by centrifugation for 1 h at 100,000×g, 4° C. 13 µM monomeric actin was polymerized in vitro by addition of 1/50 vol. Polymerization Inducer (PI; 20 mM MOPS, pH 7.5, 2 M KCl, 50 mM ATP and 100 mM MgCl$_2$) in the presence or absence of molar ratios of the peptides to actin of 0 (no peptide); 0.5 (6.5 µM peptide); 1 (13 µM peptide); 2 (26 µM peptide); 4 (52 µM peptide); and 8 (104 µM peptide) and incubated for 30 min at 30° C. The samples were centrifuged for 15 min at 10,000×g at room temperature to pellet "bundled filaments". The resulting supernatant was centrifuged for 1 h at 100,000×g at room temperature to separate F-actin filaments (G-actin) from "soluble" monomeric F-actin. The fractions were boiled in SDS-sample buffer and analyzed on a 10% SDS-Polyacrylamide gel stained with Coomassie.

Figure 6A:
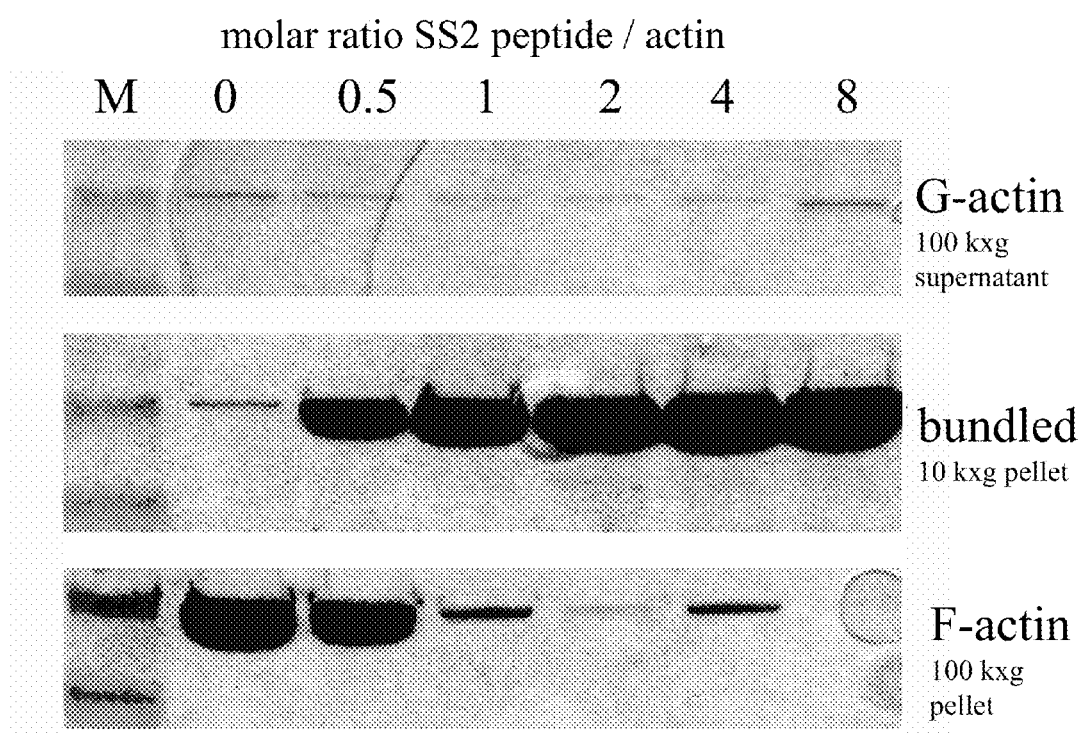
FIGS. 6A-6F are photographs of electrophoretic gels of fractions after the addition of the peptides to in vitro actin to determine the actin bundling activity of the peptides.

Referring now to FIG. 6A, the gel shows that the SS2 active peptide causes bundling of actin. SS2 active peptide was added to unpolymerized actin in vitro at a molar ratio of peptide to actin of 0, 0.5, 1, 2, 4, and 8. As shown, the active peptide SS2 causes bundling of F-actin and G-actin at a 0.5 molar ratios. Notice that at a molar ratio of 0.5, F-actin and bundled actin produce a similar size band, showing that at this molar ratio, the active peptide produces half-bundled and half-F-actin. Thus, it can be concluded that the in vitro dosage of peptide to bundle all the F-actin during polymerization, the SS2 peptide must be delivered at a 1:1 molar ratio of peptide: actin.

Figure 6B:
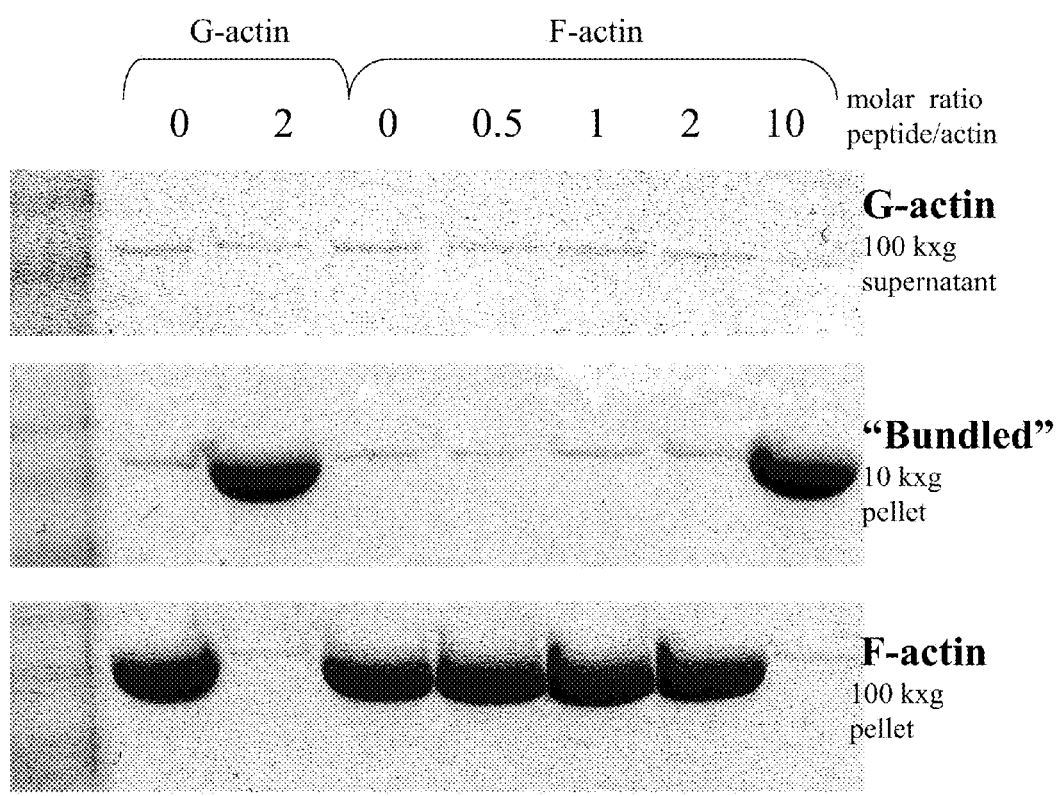

Referring now to FIG. 6B, the gel shows the effect of SS2 on polymerized actin in vitro with molar ratio of 0, 0.5, 1, 2 and 10. Purified rabbit muscle actin (2 nmol) was polymerized with SS2 in vitro for 30 min (G-actin, lanes 2 and 3) and subsequently incubated with different concentrations of SS2-peptide (0, 1, 2, 4 and 20 nmol) for another 30 min to make F-actin (lanes 4-8). Only the highest concentration of SS2 caused bundling of filamentous actin (lane 8). When SS2 was present during polymerization (G-actin, lanes 2, 3), it caused bundled actin at a molar ratio of peptide: actin of 2.

Figure 6C:
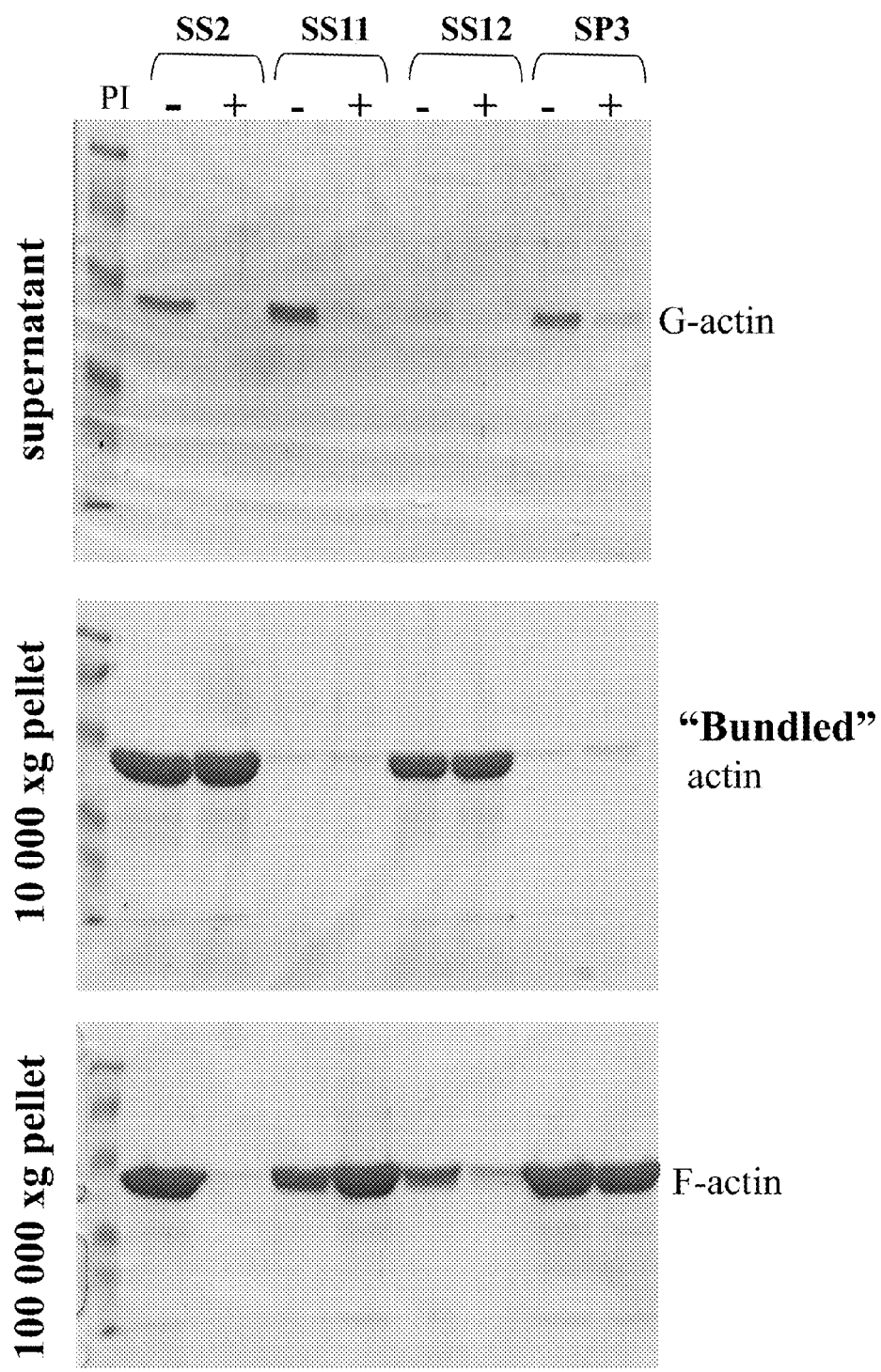

Referring now to FIG. 6C, the gel shows bundling activity of SS2, SS11, S12, SP3 peptides. "PI" means "polymerizaton induced" by the addition of a higher concentration of ATP and potassium in buffer, and whether polymerization was induced is indicated by a "+" or if polymerization was not induced is indicated by a "−". Even upon inducing polymerization, the SS11 and SP3 peptides do not produce bundled actin. The addition of the SS2 and SS12 peptides alone in a 1:1 molar ratio to actin each result in half of the actin bundled and half of the actin found in the F-actin fraction as fine and soluble actin filaments; however, upon inducing polymerization, the bulk of the actin is bundled and not found in the F-actin fraction.

Figure 6D:
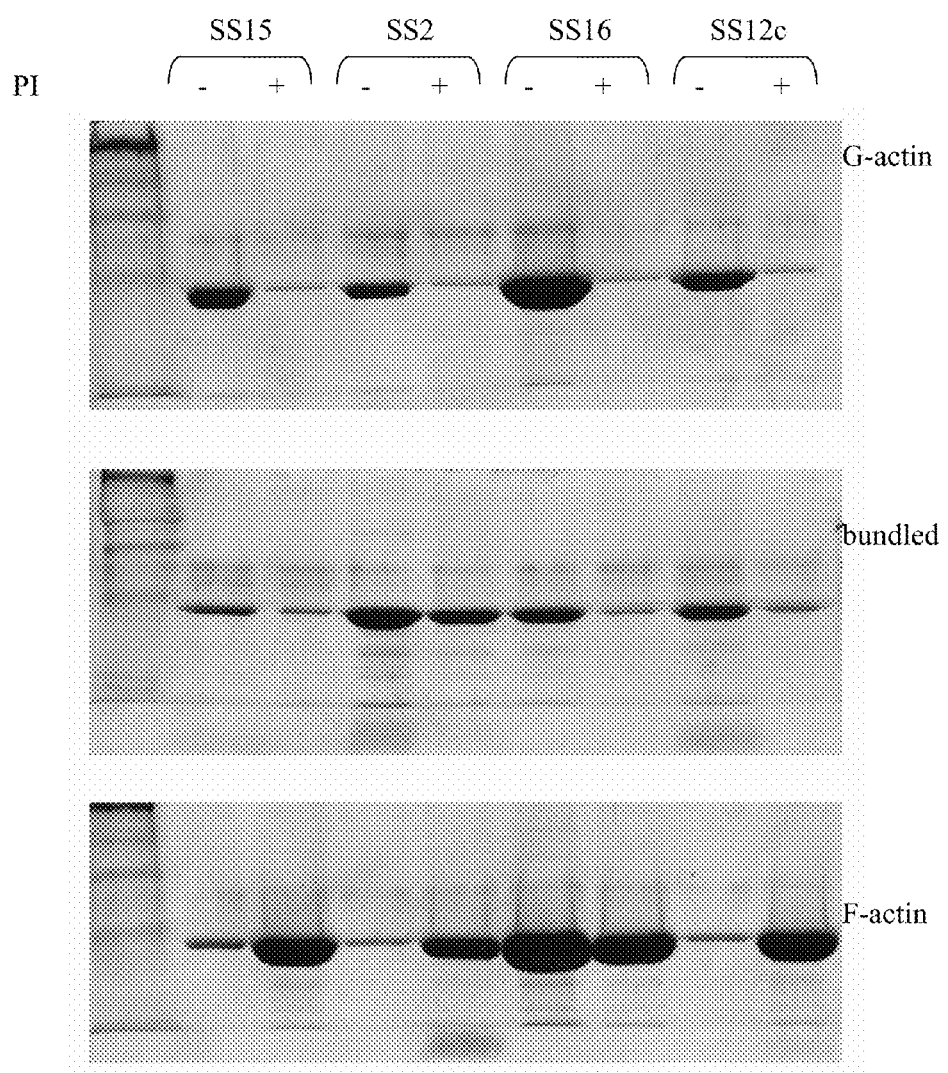

Referring now to FIG. 6D, the gel shows the bundling activity of SS15, SS2, SS16, SS12c peptides. Purified rabbit muscle actin (2 nmol) was polymerized in vitro for 30 min and subsequently incubated at molar ratio peptide:actin=1:1. Even when polymerization was induced, the SS15 and SS16 peptides did not cause bundled actin, but the bulk of the actin is found in the G-actin or the F-actin fractions. The addition of the SS2 and SS12 peptides alone in a 1:1 molar ratio to actin each result in half of the actin bundled and half of the actin found in the F-actin fraction; however, upon inducing polymerization, the bulk of the actin is bundled and not found in the F-actin fraction.

Figure 6E:
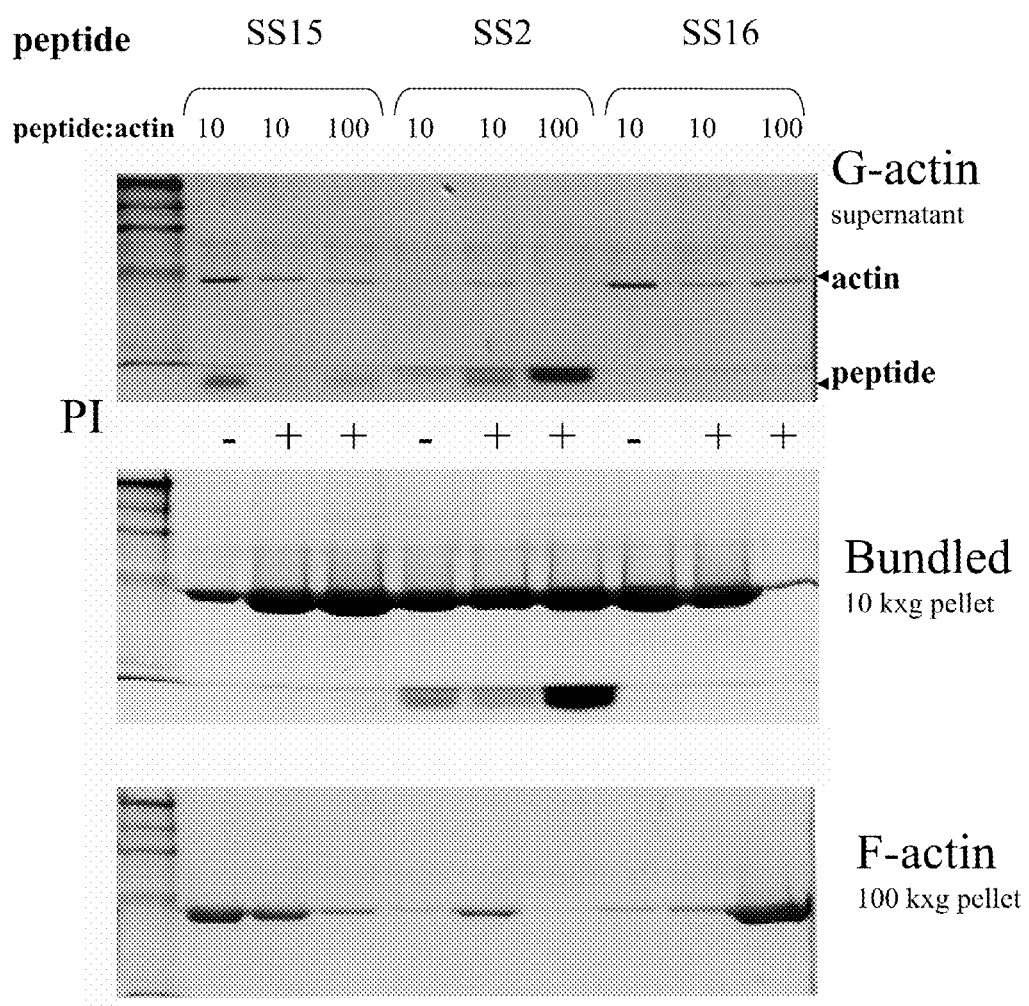

FIG. 6E is a photo of gel showing the bundling activity of SS15, SS2 and SS16 peptides in vitro after addition to unpolymerized actin with increased molar ratio of peptide:actin=10:1 and 100:1. At a molar ratio of 10 and 100, the polymerised actin is predominantly in the bundled form, with only small amounts of free F-actin after the addition of SS15 and SS16. Notice in lane 6, where the SS12 active peptide was added at a molar ratio of 100:1, there is clearly no band of free F-actin and very small bands at the lower molar ratio of 10:1, showing that the most effective peptide in bundling all the actin is likely SS12. The SS15 peptide does not completely bundle all the actin until administered at a higher molar ratio than 10. The SS16 peptide however appears to exhibit a high activity in binding actin at a molar ratio of 10 and then reaches a maximum level of activity somewhere between a molar ratio of 10 and 100, after which the activity drops off dramatically.

Figure 6F:
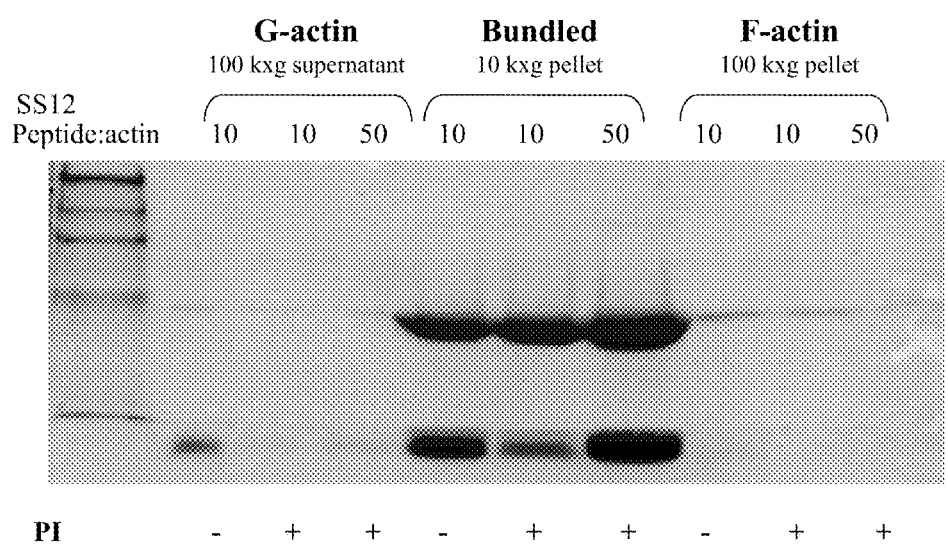

Referring now to FIG. 6F, the gel shows bundling activity of SS12 at molar ratio to actin of 10 and 50. Even at the upper levels of a molar ratio of 50, all of the actin is in the bundled form with no G-actin or free soluble F-actin. The effective peptide to actin ratio for bundling for SS16 was >16:1 and for SS15, about 16:1, as opposed to 1:1 for SS2 and SS12, the most preferred embodiments.

These experiments demonstrate that an in vitro dosage of a molar ratio of between 0.5 and 1 peptide to actin results in F-actin bundling. This represents the threshold dosage of each peptide needed in order for the peptide to cause in vitro F-actin bundling.

Example 9

Specificity of Synthetic Peptides

Figure 7:
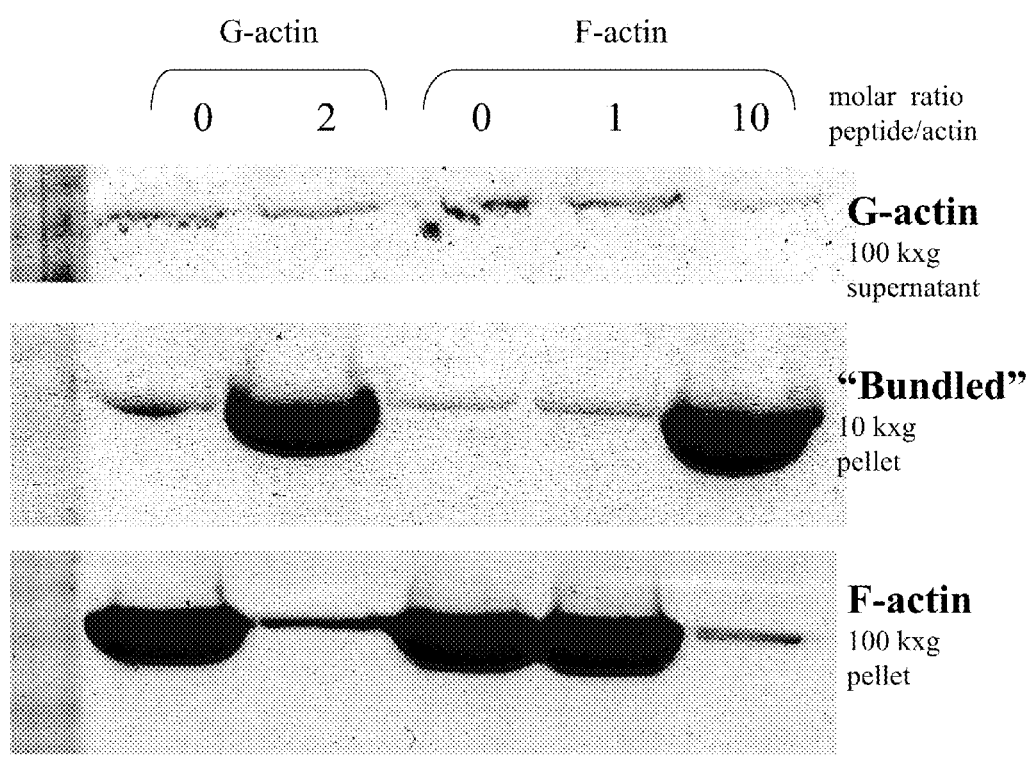
FIG. 7 is a photograph of stained gels of G-actin and F-actin showing that the bundling activity of SS2 is not affected by the addition of phalloidin.

Referring now to FIG. 7, since the SS2 sequence is specific to SuSy protein (with SS2 having some similarity to actin), we tested its effect on the well-known interaction of rabbit muscle aldolase with actin (Winter et al. 1998, Rabbit muscle aldolase was purchased from Sigma). Phalloidin could potentially interfere with the peptides of the invention since both drugs affect actin. However this gel shows that phalloidin does not have an affect on the peptide bundling activity and therefore it is possible to use both peptide and phalloidin in tandem for research applications.

Addition of SS2 peptide had no effect on aldolase precipitation in the absence of actin (FIG. 7A), but increased the amount of aldolase co-precipitating with polymerized actin (FIG. 7B). Although binding of aldolase to actin is not sucrose dependent as shown for SuSy, the presence of Sucrose in the polymerization assay caused an additional increase in the amount of aldolase bound to polymerized actin as shown by lane 6 in FIG. 7B. Rabbit muscle aldolase (1 nmol) was incubated in the absence (lanes 1-3) or presence (lanes 4-6) of rabbit muscle actin (2 nmol). Addition of 100 nmol SS2 peptide (lanes 2, 3, 5 and 6) had no effect on aldolase solubility in the absence of actin (FIG. 7A), yet increased its coprecipitation with polymerized actin (lanes 3-6, FIG. 7B). Sucrose had an additional effect on aldolase: actin binding (lanes 3, 6).

Example 10

In Vivo Administration of Active Synthetic Peptides

Peptide Preparation and Treatment Suspensions of SS12 peptide can be prepared by combining the peptide and PLURONIC F-68 block copolymer at 1:9 or 1:18 ratios of peptide to polymer, to prepare suspensions in the concentration range 0-10 mg/ml and 20 mg/ml respectively. The mixture is heated to between 150-190° C., and the peptide is solubilized in the molten polymer to obtain a clear solution. This solution is then cooled to form a solid dispersion. The solid dispersion for intrapelitoneal or intratumoral formulation can be hydrated with 2.5% dextrose solution (aqueous) by stirring at 4° C. overnight to obtain a fine suspension.

SS12 peptide is synthesized, weighed and dissolved in low salt buffer thorough mixing and sonication. Solubilizing agents can be added to the solution. Dilutions are made from this stock solution and the final excipient, 0.9% NaCl at 37° C., is added to each dose formulation just prior to dosing. The final ratio of liquid components (buffer, SS12, and saline) can be 5:5:90, respectively. Subjects having tumors are given an effective amount of the solution intratumorally, 0.1 to 0.5 ml, one to five times/week, using a syringe and a needle.

After sufficient period of peptide administration, a noticeable decrease in the tumor cell growth and cell division should be observed. Administration of the active peptides should cause the bundling of F-actin in the tumor cells, thereby prohibiting the metastasis and growth characteristic of tumor cells.

The present examples, methods, procedures, treatments, specific compounds and molecules are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference.

What is claimed is:

1. An isolated polypeptide up to 20 amino acids in length, which comprises a subsequence: SRFEVW (SEQ ID NO: 22), wherein said peptide causes 50% bundled actin and inhibits actin depolymerization when polymerized in vitro with actin.

2. An isolated polypeptide in accordance with claim 1, comprising the formula: $X_4-X_3-X_2-X_1-X_5-X_6$, where
   $X_1$ is SRFEVW,
   $X_2$ is WI,
   $X_3$ is GIVRK,
   $X_4$ is EN,
   $X_5$ is PYL, and
   $X_6$ is KK,
   wherein the polypeptide comprises $X_1$ and at least one of $X_2$ or $X_5$, and optionally at least one of $X_3$, $X_4$, and $X_6$, wherein when $X_2$, $X_3$, $X_4$, $X_5$ and $X_6$ are present, the amino acids are identical in their respective positions to those in ENGIVRKWISRFEVWPYLKK (SEQ ID NO: 24).

3. An isolated polypeptide of claim 1 which is 20 amino acids in length.

4. An isolated polypeptide of claim 1, wherein the peptide is at least 80% homologous with SEQ ID NOS: 2, 3 or 4, and said homology is over the entire length of the peptide; and
   wherein said peptide causes 50% bundled actin and inhibits actin depolymerization when polymerized in vitro with actin at a molar ratio of 100 to 1.

5. An isolated polypeptide in accordance with claim 3, wherein the peptide is polymerized with actin at a molar ratio of peptide to actin of at least 100:1.

6. An isolated polypeptide of claim 3, wherein the sequence is SEQ ID NO: 12.

7. A method for causing actin bundling and inhibition of actin depolymerization in a cell comprising the step of delivering to said cell an effective amount of an isolated peptide which comprises a subsequence: SRFEVW (SEQ ID NO: 22).

8. The method of claim 7, wherein the isolated peptide comprises at least 16 contiguous amino acids in accordance with the formula:

$$X_4-X_3-X_2-X_1-X_5-X_6, \text{ where}$$

$X_1$ is SRFEVW,
   $X_2$ is WI,
   $X_3$ is GIVRK,
   $X_4$ is EN,
   $X_5$ is PYL, and
   $X_6$ is KK,
   wherein the isolated peptide comprises $X_1$ and optionally at least one of $X_2$, $X_3$, $X_4$, $X_5$ and $X_6$, and if any of $X_2$, $X_3$, $X_4$, $X_5$ and $X_6$ are present, the amino acids are identical in their respective positions to those in ENGIVRKWISRFEVWPYLKK (SEQ ID NO: 24) and said peptide inhibits actin depolymerization when polymerized in vitro with actin.

9. A method of inhibiting growth of cells, where the method comprises administering to the cells an amount of the isolated peptide having the sequence of SEQ ID NO:26, wherein said peptide causes actin bundling and inhibits actin depolymerization.

10. The method of claim 9, wherein said isolated peptide comprises a sequence:
   EH*GIV*R*-W-----V*W (SEQ ID NO:27), where H* means H or a conservative substitution therefore, V* means V or a conservative substitution therefore, and R* means R or a conservative substitution therefore, and - means any amino acid, wherein said peptide causes actin bundling and inhibits actin depolymerization.

11. The method of claim 9, wherein said isolated peptide is SEQ ID NO: 10 or SEQ ID NO: 12.

12. The method of claim 9, wherein the administration of said isolated peptide results in about 50% of bundled actin in a molar fraction of peptide to actin of at least 100 to 1.

* * * * *